(12) United States Patent
Marzari et al.

(10) Patent No.: US 8,034,902 B2
(45) Date of Patent: Oct. 11, 2011

(54) RECOMBINANT ANTIBODIES AGAINST CD55 AND CD59 AND USES THEREOF

(75) Inventors: Roberto Marzari, Munrupino (IT); Daniele Sblattero, Trieste (IT); Francesco Tedesco, Trieste (IT)

(73) Assignee: Quark Pharmaceuticals, Inc., Fremont, CA (US)

( * ) Notice: Subject to any disclaimer, the term of this patent is extended or adjusted under 35 U.S.C. 154(b) by 375 days.

(21) Appl. No.: 11/919,816

(22) PCT Filed: May 1, 2006

(86) PCT No.: PCT/IL2006/000521
§ 371 (c)(1),
(2), (4) Date: Feb. 14, 2008

(87) PCT Pub. No.: WO2006/117782
PCT Pub. Date: Nov. 9, 2006

(65) Prior Publication Data
US 2009/0053225 A1  Feb. 26, 2009

Related U.S. Application Data

(60) Provisional application No. 60/733,950, filed on Nov. 3, 2005, provisional application No. 60/699,024, filed on Jul. 13, 2005, provisional application No. 60/677,752, filed on May 4, 2005.

(51) Int. Cl.
*C07K 16/00* (2006.01)
*C12P 21/08* (2006.01)

(52) U.S. Cl. .................. 530/387.1; 530/387.3
(58) Field of Classification Search ............... 530/387.1, 530/387.3
See application file for complete search history.

(56) References Cited

U.S. PATENT DOCUMENTS

| | | | |
|---|---|---|---|
| 4,816,567 A | 3/1989 | Cabilly et al. | |
| 4,946,778 A | 8/1990 | Ladner et al. | |
| 5,091,513 A | 2/1992 | Huston et al. | |
| 5,096,815 A | 3/1992 | Ladner et al. | |
| 5,225,539 A | 7/1993 | Winter | |
| 5,530,101 A | 6/1996 | Queen et al. | |
| 5,585,089 A | 12/1996 | Queen et al. | |
| 5,595,721 A | 1/1997 | Kaminski et al. | |
| 5,677,180 A | 10/1997 | Robinson et al. | |
| 5,693,761 A | 12/1997 | Queen et al. | |
| 5,693,762 A | 12/1997 | Queen et al. | |
| 5,736,137 A | 4/1998 | Anderson et al. | |
| 5,910,573 A | 6/1999 | Pluckthun et al. | |
| 2003/0219434 A1 | 11/2003 | Carter et al. | |
| 2006/0134110 A1* | 6/2006 | Durrant ............... | 424/144.1 |

FOREIGN PATENT DOCUMENTS

| | | |
|---|---|---|
| EP | 125023 | 11/1984 |
| EP | 171496 | 2/1986 |
| EP | 173494 | 3/1986 |
| EP | 184187 | 6/1986 |
| EP | 0552142 | 2/1991 |
| WO | WO 86/01533 | 3/1986 |
| WO | WO 90/07861 | 7/1990 |
| WO | WO 92/22653 | 12/1992 |
| WO | WO 93/15210 | 8/1993 |
| WO | WO 96/13583 | 5/1996 |
| WO | WO 96/37621 | 11/1996 |
| WO | WO 97/02671 | 1/1997 |
| WO | WO 97/32021 | 9/1997 |
| WO | WO 2004/048413 | 10/2004 |

OTHER PUBLICATIONS

Paul, Fundamental Immunology, 3rd Edition, 1993, pp. 292-295.*
Rudikoff, Proc. Natl. Acad. Sci. USA, 79(6):1979-1983, Mar. 1982.*
Colman, Research in Immunology, 145:33-36, 1994.*
Bendig, Methods: A Companion to Methods in Enzymology, 1995; 8:83-93.*
MacCallum et al, J. Mol. Biol., 262, 732-745, 1996.*
Casset et al, Biochemical and Biophysical Research Communications, 307:198-205, 2003.*
U.S. Appl. No. 08/256,790, filed Jul. 22, 1994, Pluckthun, et al.
M Better, CP Chang, RR Robinson, and Ah Horwitz Escherichia coli secretion of an active chimeric antibody fragment Science May 20, 1988: 1041-1043.
Boulianne GL, Hozumi N, Shulman MJ. Production of functional chimaeric mouse/human antibody. Nature. Dec. 13-19, 1984;312(5995):643-6.
Byers VS, Pimm MV, Scannon PJ, Pawluczyk I, Baldwin RW. Inhibition of growth of human tumor xenografts in athymic mice treated with ricin toxin A chain-monoclonal antibody 791T/36 conjugates. Cancer Res 1987. 47: 5042-5046.
Byers VS, Rodvien R, Grant K, Durrant LG, Hudson KH, Baldwin RW, Scannon PJ.Phase I study of monoclonal antibody-ricin a chain immunotoxin XomaZyme-791 in patients with metastatic colon cancer.1989, Cancer Res 49: 6153-6160.
Cabilly S, Riggs AD, Pande H, Shively JE, Holmes WE, Rey M, Perry L.J, Wetzel R, Heyneker HL.Generation of antibody activity from immunoglobulin polypeptide chains produced in *Escherichia coli*. Proc Natl Acad Sci U S A. Jun. 1984;81(11):3273-7.
Di Gaetano N, Cittera E, Nota R, Vecchi a, Grieco V, Scanziani E, Botto M, Introna M, Golay J.Complement activation determines the therapeutic activity of rituximab in vivo. J Immunol. Aug. 1, 2003;171(3):1581-7.
Gavilondo JV, Larrick JW. Antibody engineering at the millennium. Biotechniques. Jul. 2000;29(1):128-32, 134-6, 138 passim.
Gelderman KA, Tomlinson S, Ross GD, Gorter A. Complement function in mAb-mediated cancer immunotherapy. Trends Immunol. Mar. 2004;25(3):158-64.

(Continued)

*Primary Examiner* — Hong Sang
(74) *Attorney, Agent, or Firm* — John P. White; Cooper & Dunham LLP

(57) ABSTRACT

The present invention relates to recombinant antibody molecules and functional fragments thereof, useful for neutralizing the complement regulatory proteins CD55 and CD59, compositions comprising the recombinant molecules and methods of using the recombinant molecules for controlling complement resistance in cancer. The present invention further relates to heterodimeric diabody molecules comprising variable regions specific for CD55/CD59 and CD20.

14 Claims, 8 Drawing Sheets

OTHER PUBLICATIONS

Golay J, Zaffaroni L, Vaccari T, Lazzari M, Borleri GM, Bernasconi S, Tedesco F, Rambaldi A, Introna M. Biologic response of B lymphoma cells to anti-CD20 monoclonal antibody rituximab in vitro: CD55 and CD59 regulate complement-mediated cell lysis. Blood. Jun. 15, 2000;95(12):3900-8.

Golay J, Lazzari M, Facchinetti V, Bernasconi S, Borleri G, Barbui T, Rambaldi A, Introna M. CD20 levels determine the in vitro susceptibility to rituximab and complement of B-cell chronic lymphocytic leukemia: further regulation by CD55 and CD59. Blood. Dec. 1, 2001;98(12):3383-9.

Hakulinen J, Meri S. Complement-mediated killing of microtumors in vitro. Am J Pathol. Sep. 1998;153(3):845-55.

Hanke T, Szawlowski P, Randall RE. Construction of solid matrix-antibody-antigen complexes containing simian immunodeficiency virus p27 using tag-specific monoclonal antibody and tag-linked antigen. J Gen Virol. Mar. 1992;73 ( Pt 3):653-60.

Ed Harlow and David Lane "Antibodies; A Laboratory Manual" from Cold Spring Harbor Laboratory press, Dec. 1, 1988; pp. 139-149.

Hekman A, Honselaar A, Vuist WM, Sein JJ, Rodenhuis S, ten Bokkel Huinink WW, Somers R, Rümke P, Melief CJ. Initial experience with treatment of human B cell lymphoma with anti-CD19 monoclonal antibody. Cancer Immunol Immunother. 1991;32(6):364-72.

Holliger P, Prospero T, Winter G. "Diabodies": small bivalent and bispecific antibody fragments. Proc Natl Acad Sci U S A. Jul. 15, 1993;90(14):6444-8.

Liu AY, Robinson RR, Murray ED Jr, Ledbetter JA, Hellstrom I, Hellström KE. Production of a mouse-human chimeric monoclonal antibody to CD20 with potent Fc-dependent biologic activity. J Immunol. Nov. 15, 1987;139(10):3521-6.

Karpovsky B, Titus JA, Stephany DA, Segal DM Production of target-specific effector cells using hetero-cross-linked aggregates containing anti-target cell and anti-Fc gamma receptor antibodies. J Exp Med. Dec. 1, 1984;160(6):1686-701.

E Li, A Pedraza, M Bestagno, S Mancardi, R Sanchez, and O Burrone Mammalian cell expression of dimeric small immune proteins (SIP). Protein Eng. 1997 10: 731-736.

Mack M, Riethmüller G, Kufer P. A small bispecific antibody construct expressed as a functional single-chain molecule with high tumor cell cytotoxicity. Proc Natl Acad Sci U S A. Jul. 18, 1995;92(15):7021-5.

Macor P, Tripodo C, Zorzet S, Piovan E, Bossi F, Marzari R, Amadori A, Tedesco F. In vivo targeting of human neutralizing antibodies against CD55 and CD59 to lymphoma cells increases the antitumor activity of rituximab. Cancer Res. Nov. 1, 2007;67(21):10556-63.

Marzari R, Sblattero D, Macor P, Fischetti F, Gennaro R, Marks JD, Bradbury A, Tedesco F The cleavage site of C5 from man and animals as a common target for neutralizing human monoclonal antibodies: in vitro and in vivo studies. Eur J Immunol. Oct. 2002;32(10):2773-82.

Milstein C, Cuello AC Hybrid hybridomas and their use in immunohistochemistry. Nature. Oct. 6-12, 1983;305(5934):537-40.

Morrison SL, Johnson MJ, Herzenberg LA, Oi VT Chimeric human antibody molecules: mouse antigen-binding domains with human constant region domains. Proc Natl Acad Sci U S A. Nov. 1984;81(21):6851-5.

Neuberger MS, Williams GT, Fox RO. Recombinant antibodies possessing novel effector functions. Nature. Dec. 13-19, 1984;312(5995):604-8.

Press OW, Appelbaum F, Ledbetter JA, Martin PJ, Zarling J, Kidd P, Thomas ED Monoclonal antibody 1F5 (anti-CD20) serotherapy of human B cell lymphomas. Blood. Feb. 1987;69(2):584-91.

Ridgway, J.B., Presta, L.G., Carter, P., "Knobs-into-holes" engineering of antibody CH3 domains for heavy chain heterodimerization. Protein Eng. 1996. 9, 617.

Sahagan BG, Dorai H, Saltzgaber-Muller J, Toneguzzo F, Guindon CA, Lilly SP, McDonald KW, Morrissey DV, Stone BA, Davis GL, et al. A genetically engineered murine/human chimeric antibody retains specificity for human tumor-associated antigen. J Immunol. Aug. 1, 1986;137(3):1066-74.

Sblattero D, Bradbury A. Exploiting recombination in single bacteria to make large phage antibody libraries. Nat Biotechnol. Jan. 2000;18(1):75-80.

Sblattero D, Bradbury A. A definitive set of oligonucleotide primers for amplifying human V regions. Immunotechnology. Jan. 1998;3(4):271-8.

Shahied LS, Tang Y, Alpaugh RK, Somer R, Greenspon D, Weiner LM. Bispecific minibodies targeting HER2/neu and CD16 exhibit improved tumor lysis when placed in a divalent tumor antigen binding format. J Biol Chem. Dec. 24, 2004;279(52):53907-14.)

Sun LK, Curtis P, Rakowicz-Szulczynska E, Ghrayeb J, Chang N, Morrison SL, Koprowski H. Chimeric antibody with human constant regions and mouse variable regions directed against carcinoma-associated antigen 17-1A. Proc Natl Acad Sci U S A. Jan. 1987;84(1):214-8.

Verma R, Boleti E, George AJ. Antibody engineering: comparison of bacterial, yeast, insect and mammalian expression systems. J Immunol Methods. Jul. 1, 1998;216(1-2):165-81.

Vlasveld LT, Hekman A, Vyth-Dreese FA, Melief CJ, Sein JJ, Voordouw AC, Dellemijn TA, Rankin EM. Treatment of low-grade non-Hodgkin's lymphoma with continuous infusion of low-dose recombinant interleukin-2 in combination with the B-cell-specific monoclonal antibody CLB-CD19. Cancer Immunol Immunother. Jan. 1995;40(1):37-47.

Walport, 2001, Complement: Second of Two Parts. N Engl J Med, 344: 1140-1144.

Wüest T, Moosmayer D, Pfizenmaier K. Construction of a bispecific single chain antibody for recruitment of cytotoxic T cells to the tumour stroma associated antigen fibroblast activation protein. J Biotechnol. Dec. 28, 2001;92(2):159-68.

Xiong D, Xu Y, Liu H, Peng H, Shao X, Lai Z, Fan D, Yang M, Han J, Xie Y, Yang C, Zhu Z. Efficient inhibition of human B-cell lymphoma xenografts with an anti-CD20 x anti-CD3 bispecific diabody. Cancer Lett. Mar. 8, 2002;177(1):29-39.

Ziller F, Macor P, Bulla R, Sblattero D, Marzari R, Tedesco F. Controlling complement resistance in cancer by using human monoclonal antibodies that neutralize complement-regulatory proteins CD55 and CD59.. Eur J Immunol. Jul. 2005;35(7):2175-83.

PCT/IL2006/000521 International Search Report and Written Opinion issued Jul. 29, 2008.

International Preliminary Report on Patentability issued Apr. 5, 2011 in connection with International Application No. PCT/IL2006/000521.

* cited by examiner

SEQUENCE LISTING

<160> NUMBER OF SEQ ID NOS: 26

<210> SEQ ID NO 1
<211> LENGTH: 342
<212> TYPE: DNA
<213> ORGANISM: Homo sapiens

<400> SEQUENCE: 1

```
gatattgtgt tgacacagtc tccagactcc ctggctgtgt ctctgggcga gagggccacc      60
atcaactgca agtccagcca gagtgtttta tacagctcca acaataagaa ctacttagct     120
```

```
tggtaccagc agaaaccagg acagcctcct aagctgctca tttactgggc atctacccgg      180
gaatccgggg tccccgaccg attcagtggc agcgggtctg ggacagattt cactcccgcc      240
atcagcagcc tgcaggctga agatgtggca gtttattact gtcagcaata ttatagtact      300
cctcagctca ctttcggcgg agggaccaaa gtggatatca aa                        342

<210> SEQ ID NO 2
<211> LENGTH: 114
<212> TYPE: PRT
<213> ORGANISM: Homo sapiens

<400> SEQUENCE: 2

Asp Ile Val Leu Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Pro Ala
65                  70                  75                  80

Ile Ser Ser Leu Gln Ala Glu Asp Val Ala Val Tyr Tyr Cys Gln Gln
                85                  90                  95

Tyr Tyr Ser Thr Pro Gln Leu Thr Phe Gly Gly Gly Thr Lys Val Asp
            100                 105                 110

Ile Lys

<210> SEQ ID NO 3
<211> LENGTH: 62
<212> TYPE: DNA
<213> ORGANISM: Homo sapiens

<400> SEQUENCE: 3
tccggagggt cgaccataac ttcgtataat gtatactata cgaagttatc ctcgagcggt      60
ac                                                                    62

<210> SEQ ID NO 4
<211> LENGTH: 21
<212> TYPE: PRT
<213> ORGANISM: Homo sapiens

<400> SEQUENCE: 4

Ser Gly Gly Ser Thr Ile Thr Ser Tyr Asn Val Tyr Tyr Thr Lys Leu
1               5                   10                  15

Ser Ser Ser Gly Thr
            20

<210> SEQ ID NO 5
<211> LENGTH: 345
<212> TYPE: DNA
<213> ORGANISM: Homo sapiens

<400> SEQUENCE: 5
caggtacagc tgcagcagtc aggggggaggc gtggtccagc ctggggaggtc cctgggactc      60 tcctgtgcag cgtctggatt caccttcagt agctatggca tgaactgggt ccgccaggct     120
ccagggaagg ggctggagtg ggtttcatac attagtagta gtagtagtac catatactac     180
gcagactctg tgaagggccg attcaccatc tccagagaca attccaagaa cacgctgtat     240
```

```
ctgcaaatga acagcctgag agccgaggac acggctgtgt attactgtgc gagagggcct    300
ggtatggacg tctggggcca agggacaacg gtcaccgtct cttca                    345
```

<210> SEQ ID NO 6
<211> LENGTH: 114
<212> TYPE: PRT
<213> ORGANISM: Homo sapiens

<400> SEQUENCE: 6

```
Gln Val Gln Leu Gln Gln Ser Gly Gly Gly Val Val Gln Pro Gly Arg
1               5                   10                  15

Ser Leu Gly Leu Ser Cys Ala Ala Ser Gly Phe Thr Phe Ser Ser Tyr
            20                  25                  30

Gly Met Asn Trp Val Arg Gln Ala Pro Gly Lys Gly Leu Glu Trp Val
        35                  40                  45

Ser Tyr Ile Ser Ser Ser Ser Thr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Pro Gly Met Asp Val Trp Gly Gln Gly Thr Thr Val Thr
            100                 105                 110

Val Ser
```

<210> SEQ ID NO 7
<211> LENGTH: 327
<212> TYPE: DNA
<213> ORGANISM: Homo sapiens

<400> SEQUENCE: 7

```
tcgtctgagc tgactcagga gcctgctgtg tctgtggcct tgggacagac agtctcgatc     60
acgtgccaag agacagcct cagaagctat tatgcaagct ggtaccaaca gaagccagga    120
caggccccta ttcctgtcat ttatggtaaa aataaccggc cctcagggat cccagaccga    180
ttctctggct ccagctcagg aaacacagct tcgttgacca tcactggggc tcaggcggaa    240
gatgaggctg actattactg tagctcccgg gacaacagag gtacccatcg atgggtcttc    300
ggcggaggga ccaagctcac cgtccta                                        327
```

<210> SEQ ID NO 8
<211> LENGTH: 109
<212> TYPE: PRT
<213> ORGANISM: Homo sapiens

<400> SEQUENCE: 8

```
Ser Ser Glu Leu Thr Gln Glu Pro Ala Val Ser Val Ala Leu Gly Gln
1               5                   10                  15

Thr Val Ser Ile Thr Cys Gln Gly Asp Ser Leu Arg Ser Tyr Tyr Ala
            20                  25                  30

Ser Trp Tyr Gln Gln Lys Pro Gly Gln Ala Pro Ile Pro Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80
```

```
Asp Glu Ala Asp Tyr Tyr Cys Ser Ser Arg Asp Asn Arg Gly Thr His
             85                  90                  95

Arg Trp Val Phe Gly Gly Gly Thr Lys Leu Thr Val Leu
            100                 105
```

<210> SEQ ID NO 9
<211> LENGTH: 63
<212> TYPE: DNA
<213> ORGANISM: Homo sapiens

<400> SEQUENCE: 9

```
tccggagggt cgaccataac ttcgtataat gtatactata cgaagttatc ctcgagcggt    60
acc                                                                  63
```

<210> SEQ ID NO 10
<211> LENGTH: 21
<212> TYPE: PRT
<213> ORGANISM: Homo sapiens

<400> SEQUENCE: 10

```
Ser Gly Gly Ser Thr Ile Thr Ser Tyr Asn Val Tyr Tyr Thr Lys Leu
1               5                  10                  15

Ser Ser Ser Gly Thr
            20
```

<210> SEQ ID NO 11
<211> LENGTH: 360
<212> TYPE: DNA
<213> ORGANISM: Homo sapiens

<400> SEQUENCE: 11

```
caggtcaact taagggagtc tgggggaggc ttggtacagc ctggcaggtc cctgagactc     60
tcctgtgcag cctctggatt cacctttgat gattatgcca tgcactgggt ccggcaagct    120
ccagggaagg gcctggagtg ggtctcaggt attagttgga atagtggtag cataggctat    180
gcggactctg tgaagggccg atttaccatc tccagagaca acgccaagaa ctccctgtat    240
ctgcaaatga acagtctgag agctgaggac acggccttgt attactgtgc aaaagatagg    300
tccgatcgtg cagactcctg gactactggg gcctgggaa ccctggtcac cgtctcctca     360
```

<210> SEQ ID NO 12
<211> LENGTH: 119
<212> TYPE: PRT
<213> ORGANISM: Homo sapiens

<400> SEQUENCE: 12

```
Gln Val Asn Leu Arg Glu Ser Gly Gly Gly Leu Val Gln Pro Gly Arg
1               5                  10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95
```

Ala Lys Asp Arg Ser Asp Arg Gly Arg Leu Leu Asp Tyr Trp Gly Leu
            100                 105                 110

Gly Thr Leu Val Thr Val Ser
        115

<210> SEQ ID NO 13
<211> LENGTH: 30
<212> TYPE: DNA
<213> ORGANISM: Homo sapiens

<400> SEQUENCE: 13
cgggacaaca gaggtaccca tcgatgggtc                               30

<210> SEQ ID NO 14
<211> LENGTH: 12
<212> TYPE: PRT
<213> ORGANISM: Homo sapiens

<400> SEQUENCE: 14

Ser Ser Arg Asp Asn Arg Gly Thr His Arg Trp Val
1               5                   10

<210> SEQ ID NO 15
<211> LENGTH: 33
<212> TYPE: DNA
<213> ORGANISM: Homo sapiens

<400> SEQUENCE: 15
gataggtccg atcgtggcag actccttgac tac                           33

<210> SEQ ID NO 16
<211> LENGTH: 11
<212> TYPE: PRT
<213> ORGANISM: Homo sapiens

<400> SEQUENCE: 16

Asp Arg Ser Asp Arg Gly Arg Leu Leu Asp Tyr
1               5                   10

<210> SEQ ID NO 17
<211> LENGTH: 30
<212> TYPE: DNA
<213> ORGANISM: Homo sapiens

<400> SEQUENCE: 17
cagcaatatt atagtactcc tcagctcact                               30

<210> SEQ ID NO 18
<211> LENGTH: 10
<212> TYPE: PRT
<213> ORGANISM: Homo sapiens

<400> SEQUENCE: 18

Gln Gln Tyr Tyr Ser Thr Pro Gln Leu Thr
1               5                   10

<210> SEQ ID NO 19
<211> LENGTH: 18
<212> TYPE: DNA
<213> ORGANISM: Homo sapiens

<400> SEQUENCE: 19
gggcctggta tggacgtc                                            18

```
<210> SEQ ID NO 20
<211> LENGTH: 6
<212> TYPE: PRT
<213> ORGANISM: Homo sapiens

<400> SEQUENCE: 20

Gly Pro Gly Met Asp Val
1               5

<210> SEQ ID NO 21
<211> LENGTH: 34
<212> TYPE: DNA
<213> ORGANISM: Homo sapiens

<400> SEQUENCE: 21
atccgagtgc acacctgtgg agagaaaggc aaag                              34

<210> SEQ ID NO 22
<211> LENGTH: 34
<212> TYPE: DNA
<213> ORGANISM: Homo sapiens

<400> SEQUENCE: 22
tcctcagcgc gcggctctgg tggcagaccg aagg                              34

<210> SEQ ID NO 23
<211> LENGTH: 41
<212> TYPE: DNA
<213> ORGANISM: Homo sapiens

<400> SEQUENCE: 23
aggcggcgcg cgacaaaact cacacatgcc caccgtgccc a                      41

<210> SEQ ID NO 24
<211> LENGTH: 94
<212> TYPE: DNA
<213> ORGANISM: Homo sapiens

<400> SEQUENCE: 24
acgtcgatcg cctgctgaat tcttaagtac tatccaggcc cagcagtggg tttgggattg   60
gtttgccact agttttaccc ggggacaggg agag                              94

<210> SEQ ID NO 25
<211> LENGTH: 2525
<212> TYPE: DNA
<213> ORGANISM: Homo sapiens

<400> SEQUENCE: 25
tctagatgcc accatgggct ggagcctgat cctcctgttc ctcgtcgctg tggctacagg   60 taagggctc acagtagcag gcttgaggtc tggacatata tatgggtgac aatgacatcc   120
actttgcctt tctctccaca ggtgtgcact cggcgcgcga caaaactcac acatgcccac   180
cgtgcccagc acctgaactc ctggggggac cgtcagtctt cctcttcccc ccaaaaccca   240
aggacaccct catgatctcc cggacccctg aggtcacatg cgtggtggtg gacgtgagcc   300
acgaagaccc tgaggtcaag ttcaactggt acgtggacgg cgtggaggtg cataatgcca   360
agacaaagcc gcgggaggag cagtacaaca gcacgtaccg tgtggtcagc gtcctcaccg   420
tcctgcacca ggactggctg aatggcaagg agtacaagtg caaggtctcc aacaaagccc   480
tcccagcccc catcgagaaa accatctcca aagccaaagg gcagccccga gaaccacagg   540
tgtacaccct gcccccatcc cgggaggaga tgaccaagaa ccaggtcagc ctgacctgcc   600
```

```
tggtcaaagg cttctatccc agcgacatcg ccgtggagtg ggagagcaat gggcagccgg    660
agaacaacta caagaccacg cctcccgtgc tggactccga cggctccttc ttcctcacca    720
gcaagctcac cgtggacaag agcaggtggc agcagggaa cgtcttctca tgctccgtga    780
tgcatgaggc tctgcacaac cactacacgc agaagagcct ctccctgtcc ccgggtaaaa    840
ctagtggcaa accaatccca aacccactgc tgggcctgga tagtactagg gccaagagag    900
caccggtgaa acagactttg aattttgacc ttctcaagtt ggcgggagac gtggagtcca    960
acccagggcc catggatttt caggtgcaga ttatcagctt cctgctaatc agtgcttcag   1020
tcataatgtc cagagggcaa attgttctct cccagtctcc agcaatcctg tctgcatctc   1080
caggggagaa ggtcacaatg acttgcaggg ccagctcaag tgtaagttac atccactggt   1140
tccagcagaa gccaggatcc tcccccaaac cctggattta tgccacatcc aacctggctt   1200
ctggagtccc tgttcgcttc agtggcagtg gtctgggac ttcttactct ctcacaatca   1260
gcagagtgga ggctgaagat gctgccactt attactgcca gcagtggact agtaacccac   1320
ccacgttcgg agggggacc aagctggaaa tcaaatccgg agggtcgacc ataacttcgt   1380
ataatgtata ctatacgaag ttatcctcga gcggtaccca ggtacaactg cagcagcctg   1440
gggctgagct ggtgaagcct ggggcctcag tgaagatgtc ctgcaaggct tctggctaca   1500
catttaccag ttacaatatg cactgggtaa acagacacc tggtcgggc ctggaatgga   1560 ttggagctat ttatcccgga aatggtgata cttcctacaa tcagaagttc aaaggcaagg   1620
ccacattgac tgcagacaaa tcctccagca gcctacat gcagctcagc agcctgacat   1680
ctgaggactc tgcggtctat tactgtgcaa gatcgactta ctacggcggt gactggtact   1740
tcaatgtctg gggcgcaggg accacggtca ccgtctctgc agctagcgac aaaactcaca   1800
catgcccacc gtgcccagca cctgaactcc tggggggacc gtcagtcttc ctcttccccc   1860
caaaacccaa ggacaccctc atgatctccc ggacccctga ggtcacatgc gtggtggtgg   1920
acgtgagcca cgaagaccct gaggtcaagt tcaactggta cgtggacggc gtggaggtgc   1980
ataatgccaa gacaaagccg cgggaggagc agtacaacag cacgtaccgt gtggtcagcg   2040
tcctcaccgt cctgcaccag gactggctga atggcaagga gtacaagtgc aaggtctcca   2100
acaaagccct cccagccccc atcgagaaaa ccatctccaa agccaaaggg cagccccgag   2160
aaccacaggt gtacaccctg cccccatccc gggaggagat gaccaagaac caggtcagcc   2220
tgtactgcct ggtcaaaggc ttctatccca gcgacatcgc cgtggagtgg gagagcaatg   2280
ggcagccgga gaacaactac aagaccacgc ctcccgtgct ggactccgac ggctccttct   2340
tcctctatag caagctcacc gtggacaaga gcaggtggca gcagggaac gtcttctcat   2400 gctccgtgat gcatgaggct ctgcacaacc actacacgca gaagagcctc tccctgtccc   2460
cgggtaaaac tagtggcaaa ccaatcccaa acccactgct gggcctggat agtacttaaa   2520
agctt                                                              2525
```

<210> SEQ ID NO 26
<211> LENGTH: 24
<212> TYPE: PRT
<213> ORGANISM: Homo sapiens
<400> SEQUENCE: 26

```
Ala Pro Val Lys Gln Thr Leu Asn Phe Asp Leu Leu Lys Leu Ala Gly
1               5                   10                  15

Asp Val Glu Ser Asn Pro Gly Pro
            20
```

RECOMBINANT ANTIBODIES AGAINST CD55 AND CD59 AND USES THEREOF

This application is a §371 national stage of PCT International Application No. PCT/IL2006/000521, filed May 1, 2006, and claims the benefit of U.S. Provisional Applications Nos. 60/733,950, filed Nov. 3, 2005; 60/699,024, filed Jul. 13, 2005; and 60/677,752, filed May 4, 2005, the contents of all of which are hereby incorporated by reference in their entirety into this application. Throughout this application various patent and scientific publications are cited. The disclosures for these publications in their entireties are hereby incorporated by reference into this application to more fully describe the state of the art to which this invention pertains.

FIELD OF THE INVENTION

The present invention relates to immunoglobulins and functional fragments thereof, useful for neutralizing the complement regulatory proteins CD55 and CD59, compositions comprising the immunoglobulins and methods of using the immunoglobulins therapeutically, in particular for controlling complement resistance in cancer.

BACKGROUND OF THE INVENTION

The complement (C) system is an essential component of innate immunity and is actively involved in the host defense against infectious agents and in the removal of immune complexes and apoptotic cells (Walport, 2001, N Engl J Med, 344: 1140-1144). Tumor cells may also be potential target of C since C4, C3 and C5b-9 are deposited on breast and thyroid carcinoma. The C system has a definite potential advantage over cytotoxic cells as a defense system because it is made of soluble molecules that can easily reach the tumor site and diffuse inside the tumor mass. Moreover, C components are readily available as a first line of defense because they are synthesized locally by many cell types, including macrophages, fibroblasts and endothelial cells, and the amount of components released is regulated by cytokines and other pro-inflammatory molecules.

The C system requires an activation process to release the biologically active products that are capable of recognizing and attacking neoplastic cells. The system can be activated by tumor cells, as for example B lymphoblastoid cells that trigger the C sequence through the alternative pathway. Some glioma cell lines bind mannose binding lectin and activate the lectin pathway. Apoptotic tumor cell lines can also activate the alternative pathway by expressing a surface molecule undetectable on normal cells. However, antibody-mediated activation of the classical pathway represents the most efficient way to target C activation products to tumor cells in sufficient quantity to cause cell damage. Unfortunately, only low-titer and low-affinity antibodies (Abs) to tumor antigens are usually detected in cancer patients. These Abs are poor C activators and are therefore unlikely to mediate C-dependent cytotoxicity (CDC) of tumor cells.

A renewed interest in C as an important effector system for tumor cell cytotoxicity has been raised by the introduction of chimeric or humanized monoclonal Abs in cancer therapy. Several Abs have been developed and some of them are currently used in the treatment of patients with hematological malignancies and solid tumors (Gelderman, et al., 2004, Trends Immunol. 25: 158-164). Rituximab® is the most extensively studied chimeric Ab and has been used for the treatment of low-grade/follicular non-Hodgkin's lymphomas as a single therapeutic agent with a success rate of about 50%. This mouse/human chimeric Ab is directed against CD20 expressed on mature B lymphocytes and on 90% of B-cell non-Hodgkin's lymphomas and contains the C-fixing human IgG1 and κ regions.

The mechanisms implicated in the killing of lymphoma cell lines mediated by Rituximab include a direct apoptotic effect of the Abs, Abs-dependent Cell Cytotoxicity (ADCC) and CDC. However, these three mechanisms may not be equally effective in inducing tumor cell death in vivo. Analysis of primary non-Hodgkin's lymphoma cells for their susceptibility to Rituximab-mediated killing showed that Rituximab had a negligible apoptotic effect. Furthermore, the susceptibility of all the cells examined for ADCC did not correlate with the clinical response to the Abs, whereas the in vitro cell-sensitivity to CDC was found to be the best predictor of the in vivo effect of Rituximab. Additional support for the important role played by CDC in mediating the therapeutic effect of Rituximab was provided by Di Gaetano and colleagues (Di Gaetano et al., 2003, J Immunol. 171: 1581-1587) who showed that Rituximab inhibited the growth of a murine lymphoma transfected with CD20 in C sufficient mice, but not in C1q deficient mice.

A major limitation to the therapeutic efficacy of mAbs is represented by the surface overexpression of the C regulatory proteins (CRPs) CD46, CD55 and CD59 that inhibit the C sequence at different steps of activation. These CRPs restrict the susceptibility of tumor cells to Abs-dependent CDC and provide a mechanism of evasion for tumor cells to resist C attack. Golay and colleagues (Golay et al., 2001, Blood 98: 3383-3389) analyzed several B lymphoma cell lines and a few samples of fresh follicular non-Hodgkin's lymphoma cells for their sensitivity to CDC induced by Rituximab and observed that C resistance was dependent on the expression level of CD55 and CD59. The same group later extended these findings to freshly isolated B cells from patients with chronic lymphocytic leukemia. In both of these studies lyses of the C-resistant cells was restored by the addition of neutralizing antibodies to CD55 and CD59 suggesting that blocking the inhibitory activity of the two CRPs would enhance the therapeutic effect of Rituximab.

Patent application US2003219434 discloses a method for making antibodies, for example antibodies directed against decay accelerating factor (DAF) (CD55), using a naive antibody phage library. The human antibody LU30 is suggested for use in assessing overexpression of DAF and for treatment of lung cancer particularly when combined with cytotoxic agents. Patent application WO2004048413 discloses the use of an antibody which binds to both complementary determining region SCR1 and SCR2 of CD55 in the treatment of tumors and leukaemia. Patent application WO9732021 describes the production of the anti-idiotype antibody 105AD7 and potential therapeutic uses of the antibody.

Therapeutic studies with antibodies directed to complementary determining region (SCRs) have been limited to immunoconjugated molecules (EP0552142, and Byers et al., 1987, Cancer Res 47: 5042-5046). Byers et al., describes studies with 791T/36 linked to ricin A chain and showed significantly inhibition of tumor growth in athymic mice. 791T/36-RTA was therefore screened in a phase I clinical trial in advanced colorectal cancer patients (Byers et al., 1989, Cancer Research 49: 6153-6160). However the trial was unsuccessful due to dose limiting toxicity.

Despite the evident progress, there remains a continued need for improved molecules able to elicit an immune response to human cancer cells in general and to cancer cells positive for CD55 and CD59 overexpression in particular.

SUMMARY OF THE INVENTION

The present invention provides specific recombinant antibody molecules and antibody fragments which bind to one or more of the C regulatory proteins CD55 and CD59, and modulate activation of the complement system.

The present invention further provides a method of neutralization of one or more of the C regulatory proteins CD55 and CD59 comprising administration of recombinant antibody molecules or antibody fragments which specifically bind to one or more of the C regulatory proteins CD55 and CD59. By neutralizing one or more of the C regulatory proteins CD55 and CD59, complement activation is facilitated. Accordingly, the invention provides a method for treatment of cancer comprising administration of antibodies or antibody fragments which specifically bind to one or more of the C regulatory proteins CD55 and CD59.

The present invention further provides a pharmaceutical composition comprising as an active ingredient a recombinant antibody molecule or antibody fragment of the invention useful for treating cancer. The present invention additionally provides a method for enhancing complement activation in the tissues of subjects in need thereof by exposure to recombinant antibody molecules or antibody fragments capable of neutralizing one or more of the C regulatory proteins CD55 and CD59.

According to one aspect, the present invention provides a molecule comprising at least the antigen binding portion of a recombinant antibody which has specific binding affinity for one or more of the C regulatory proteins CD55 and CD59, and which is useful for treating cancer. Without wishing to be bound by any theory or mechanism of action, it is now disclosed that the preferred antibodies of the invention neutralize the complement inhibitory activity of one or more of the C regulatory proteins CD55 and CD59.

According to certain embodiments, the present invention provides a recombinant antibody molecule comprising one or more of the CDR3 variable regions of SEQ ID NO: 14, 16, 18 or 20 of the recombinant antibody. This molecule may be encoded by a polynucleotide comprising SEQ ID NO: 13, 15, 17 or 19 respectively.

The present invention also provides a recombinant antibody molecule comprising $V_L$ and $V_H$ regions selected from SEQ ID NO: 2 and SEQ ID NO: 6 respectively. The molecule may further comprise a linker consisting of SEQ ID NO: 4. This molecule may be encoded by a polynucleotide (e.g. DNA) comprising SEQ ID NO: 1 or 5 respectively and the linker may be encoded by a polynucleotide comprising SEQ ID NO: 3.

The present invention additionally provides a recombinant antibody molecule comprising $V_L$ and $V_H$ regions selected from SEQ ID NO: 8 and SEQ ID NO: 12 respectively. The molecule may further comprise a linker consisting of SEQ ID NO: 10. This molecule may be encoded by a polynucleotide (e.g. DNA) comprising SEQ ID NO: 7 or 11 respectively and the linker may be encoded by a polynucleotide comprising SEQ ID NO: 9.

The molecules of the invention include recombinant antibody molecules or antigen binding fragments thereof. According to one embodiment, the present invention provides cloned human single-chain antibody fragments (scFv), which bind to CD55 or CD59 and control the complement resistance in cancer. According to another embodiment, the present invention provides a recombinant antibody comprising one or more of the sequences of SEQ ID NO: 2, 6, 8, and 12. According to a further embodiment, the present invention provides a recombinant antibody encoded by one or more of the nucleic acid sequences of SEQ ID NO: 1, 5, 7 and 11.

According to another embodiment, the present invention provides a recombinant antibody which binds to CD59 and comprises $V_L$ and $V_H$ regions having SEQ ID NO: 2 and 6, respectively. The recombinant antibody may further comprise a linker consisting of SEQ ID NO: 4.

According to another embodiment, the present invention provides a recombinant antibody which binds to CD55 and comprises $V_L$ and $V_H$ regions having SEQ ID NO: 8 and 12, respectively. The recombinant antibody may further comprise a linker consisting of SEQ ID NO: 10. According to another embodiment the present invention provides a miniantibody (MB); in a particular embodiment the miniantibody was produced by genetic fusion of the anti-CD55 or anti-CD59 scFv to human IgG1 domains in particular Hinge-CH2 domains.

According to another aspect of the present invention, polynucleotides encoding molecules which bind to CD55 and/or CD59 and enhance the complement system activation are provided.

According to certain embodiments the present invention provides an isolated nucleic acid molecule, comprising one or more of the nucleic acid sequences of SEQ ID NO: 1, 5, 7, and 11, or a nucleotide sequence hybridizing under high stringency conditions thereto. According to one embodiment of the present invention, an expression vector comprising the nucleic acid molecule is provided. According to another embodiment of the present invention, the host cell transformed with the vector is provided.

A further aspect of the present invention provides a pharmaceutical composition comprising as an active ingredient the recombinant antibody molecules of the present invention useful for treating cancerous diseases. The molecules of the invention may be administered alone or in combination with one or more further active agents. Thus, the present invention further provides products comprising antibody molecules, which bind to CD55 and/or CD59 and an active agent as a combined preparation for simultaneous, separate or sequential use in the treatment of cancer. According to one preferred embodiment, the additional active agent is an antibody. According to a specific preferred embodiment, the additional antibody is a B cell target antibody, e.g., anti-CD20, anti-CD22, anti-CD19 or anti-CD40. Specifically preferred is an anti-CD20 antibody, i.e. an antibody which is specific for the CD20 epitope on cancer cells (e.g. Rituximab). The combination of anti CD55 and/or CD59 antibodies with anti CD20 antibodies in a combined composition is advantageous in order to trigger apoptosis in cancer cells overexpressing both CD20 and CD55/CD59. According to this specific example, the combined composition of anti CD55 and/or CD59 antibodies with anti CD20 antibodies comprises either separate antibody molecules or bispecific antibodies such as quadroma molecules, chemically crosslinked F(ab)2 molecules, single chain bispecific antibody molecules or diabodies.

In one embodiment of the present invention, the cancerous disease is selected from lymphoma, leukemia, colorectal, breast, ovarian, cervical, gastric, lung, liver, skin, bladder and myeloid (e.g. bone marrow) cancer. In another embodiment, the lymphoma is selected from B-cell lymphoma, thymic lymphoma, Hodgkin lymphoma, non-Hodgkin's lymphoma and T-cell lymphoma.

The therapies of the present invention are especially suitable for treating a wide range of lymphomas, including but not limited to low grade/follicular non-Hodgkin's lymphoma (NHL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL and Waldenstrom's Macroglobulinemia, chronic leukocytic leukemia, acute myelogenous leukemia, acute lymphoblastic leukemia, chronic lymphocytic leukemia, chronic myelogenous leukemia, lymphoblastic leukemia, lymphocytic leukemia, monocytic leukemia, myelogenous leukemia, and promyelocytic leukemia. Preferred targeted diseases are non-Hodgkin's lymphoma (NHL), and particularly low-grade, follicular NHL.

The compositions of the present invention are also useful for treating solid, non-hematologic (non-lymphoid) cancers, including by way of example, colorectal cancer, liver cancer, and other digestive cancers, breast cancer, esophageal cancer, head and neck cancer, lung cancer, ovarian cancer, prostate cancer and testicular cancer. These cancers may be in early, intermediate or advanced stages, e.g. metastasis.

A still further aspect of the present invention provides methods for treating the aforementioned cancerous diseases by administering a therapeutically effective dose of a pharmaceutical composition comprising an recombinant antibody molecule of the present invention to a subject in need thereof.

In a preferred embodiment, the present invention provides a method of treating a B cell lymphoma in a patient comprising administering to said patient a therapeutically effective amount of the anti CD55 and/or CD59 recombinant antibody molecules simultaneously with or consecutively with in either order an anti-CD20 antibody.

The present invention further provides a method for enhancing the complement activation in a subject in need thereof, comprising administering a therapeutically effective dose of the pharmaceutical composition thereby neutralizing one or more of the C regulatory proteins CD55 and CD59.

DETAILED DESCRIPTION OF THE INVENTION

Figure 1:
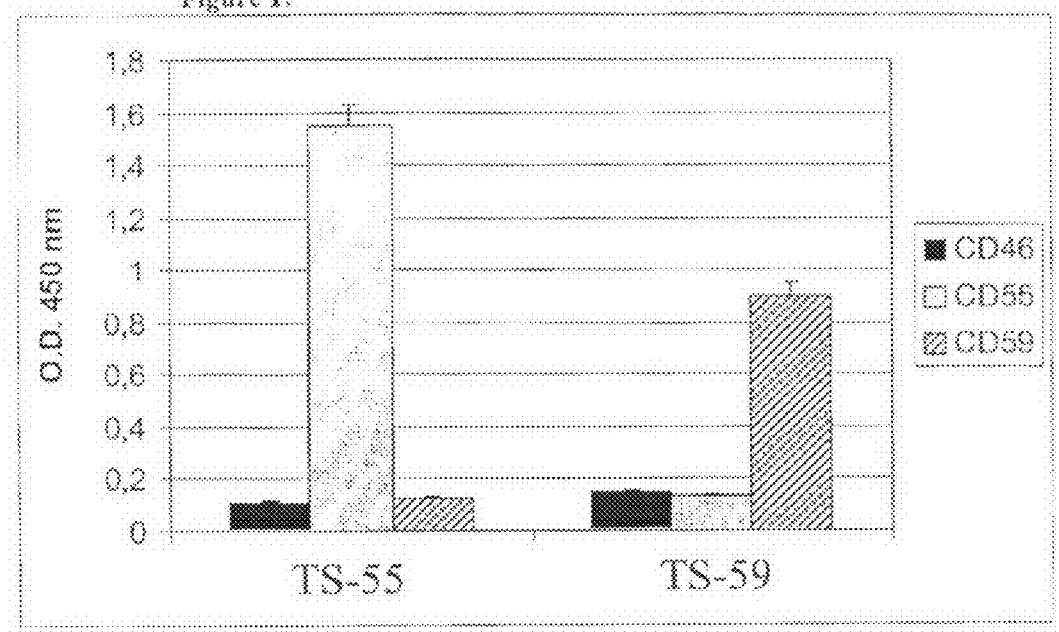
FIG. 1 shows the control of specificity of TS-55 and TS-59. Phage ELISA of 2 selected scFv: TS-55 anti-CD55 and TS-59 anti-CD59. Microtiter plates were coated with 100 µl of the various CRPs (10 µg/ml) followed by 100 µl of phage suspension in MPBS. Anti-M13 peroxidase conjugated mAb was used as a secondary antibody. Data represent mean values±SD of three different experiments.

The present invention relates to recombinant antibody molecules and fragments thereof, comprising at least an antigen-binding portion of CD55 and/or CD59. The present invention relates specifically to recombinant cloned human single-chain antibody fragment (scFv) against CD55 or CD59 which modulate complement activation. The present invention is based on the discovery that human antibodies against CD55 and/or CD59 are useful in overcoming the resistance of cancer cells to complement attack.

Molecules, including antibodies and fragments thereof, comprising at least an antigen binding portion of CD55 or CD59 antibody are useful for the development of anticancer therapeutic agents.

Antibodies

Antibodies, or immunoglobulins, comprise two heavy chains linked together by disulfide bonds and two light chains, each light chain being linked to a respective heavy chain by disulfide bonds in a "Y" shaped configuration. Proteolytic digestion of an antibody yields Fv (Fragment variable and Fc (fragment crystalline) domains. The antigen binding domains, Fab', include regions where the polypeptide sequence varies. The term F(ab')$_2$ represents two Fab' arms linked together by disulfide bonds. The central axis of the antibody is termed the Fc fragment. Each heavy chain has at one end a variable domain (VH) followed by a number of constant domains (CH). Each light chain has a variable domain (VL) at one end and a constant domain (CL) at its other end, the light chain variable domain being aligned with the variable domain of the heavy chain and the light chain constant domain being aligned with the first constant domain of the heavy chain (CH1). The variable domains of each pair of light and heavy chains form the antigen binding site. The domains on the light and heavy chains have the same general structure and each domain comprises four framework regions, whose sequences are relatively conserved, joined by three hypervariable domains known as complementarity determining regions (CDR1-3). These domains contribute specificity and affinity of the antigen binding site.

The isotype of the heavy chain (gamma, alpha, delta, epsilon or mu) determines immunoglobulin class (IgG, IgA, IgD, IgE or IgM, respectively). The light chain is either of two isotypes (kappa,κ or lambda,λ) found in all antibody classes.

It should be understood that when the terms "antibody" or "antibodies" are used, this is intended to include intact antibodies, such as polyclonal antibodies or monoclonal antibodies (mAbs), as well as proteolytic fragments thereof such as the Fab or F(ab')$_2$ fragments. Further included within the scope of the invention are chimeric antibodies; human and humanized antibodies; recombinant and engineered antibodies, and fragments thereof. Furthermore, the DNA encoding the variable region of the antibody can be inserted into the DNA encoding other antibodies to produce chimeric antibodies (see, for example, U.S. Pat. No. 4,816,567). Single chain antibodies fall within the scope of the present invention. Single chain antibodies can be single chain composite polypeptides having antigen binding capabilities and comprising amino acid sequences homologous or analogous to the variable regions of an immunoglobulin light and heavy chain (linked VH-VL or single chain Fv (ScFv)). Both $V_H$ and $V_L$ may copy natural monoclonal antibody sequences or one or both of the chains may comprise a CDR-FR construct of the type described in U.S. Pat. No. 5,091,513, the entire contents of which are hereby incorporated herein by reference. The separate polypeptides analogous to the variable regions of the light and heavy chains are held together by a polypeptide linker. Methods of production of such single chain antibodies, particularly where the DNA encoding the polypeptide structures of the $V_H$ and $V_L$ chains are known, may be accomplished in accordance with the methods described, for example, in U.S. Pat. Nos. 4,946,778, 5,091,513 and 5,096,815, the entire contents of each of which are hereby incorporated herein by reference.

Additionally, CDR grafting may be performed to alter certain properties of the antibody molecule including affinity or specificity. A non-limiting example of CDR grafting is disclosed in U.S. Pat. No. 5,225,539.

A "molecule having the antigen-binding portion of an antibody" as used herein is intended to include not only intact immunoglobulin molecules of any isotype and generated by any animal cell line or microorganism, but also the antigen-binding reactive fraction thereof, including, but not limited to, the Fab fragment, the Fab' fragment, the F(ab')$_2$ fragment, the variable portion of the heavy and/or light chains thereof, Fab miniantibodies (see WO 93/15210, U.S. patent application Ser. No. 08/256,790, WO 96/13583, U.S. patent application Ser. No. 08/817,788, WO 96/37621 and U.S. patent application Ser. No. 08/999,554, the entire contents of which are incorporated herein by reference) and chimeric or single-chain antibodies incorporating such reactive fraction, as well as any other type of molecule or cell in which such antibody reactive fraction has been physically inserted, such as a chimeric T-cell receptor or a T-cell having such a receptor, or molecules developed to deliver therapeutic moieties by means of a portion of the molecule containing such a reactive fraction. Such molecules may be provided by any known technique, including, but not limited to, enzymatic cleavage, peptide synthesis or recombinant techniques.

The term "Fc" as used herein is meant as that portion of an immunoglobulin molecule (Fragment crystallizable) that mediates phagocytosis, triggers inflammation and targets Ig to particular tissues; the Fc portion is also important in complement activation.

The term "epitope" is meant to refer to that portion of any molecule capable of being bound by an antibody or a fragment thereof which can also be recognized by that antibody. Epitopes or antigenic determinants usually consist of chemically active surface groupings of molecules such as amino acids or sugar side chains and have specific three-dimensional structural characteristics as well as specific charge characteristics.

An "antigen" is a molecule or a portion of a molecule capable of being bound by an antibody which is additionally capable of inducing an animal to produce antibody capable of binding to an epitope of that antigen. An antigen may have one or more than one epitope. The specific reaction referred to above is meant to indicate that the antigen will react, in a highly selective manner, with its corresponding antibody and not with the multitude of other antibodies which may be evoked by other antigens.

A monoclonal antibody (mAb) is a substantially homogeneous population of antibodies to a specific antigen. MAbs may be obtained by methods known to those skilled in the art. See, for example Kohler et al (1975); U.S. Pat. No. 4,376,110; Ausubel et al (1987-1999); Harlow et al (1988); and Colligan et al (1993), the contents of which references are incorporated in their entireties herein by reference. The mAbs of the present invention may be of any immunoglobulin class including IgG, IgM, IgE, IgA, and any subclass thereof. A hybridoma producing a mAb may be cultivated in vitro or in vivo. High titers of mAbs can be obtained by in vivo production where cells from the individual hybridomas are injected intraperitoneally into pristine-primed Balb/c mice to produce ascites fluid containing high concentrations of the desired mAbs. MAbs of isotype IgM or IgG may be purified from such as cites fluids, or from culture supernatants, using column chromatography or other methods well known to those of skill in the art.

Chimeric antibodies are antibodies, the different portions of which are derived from different animal species, such as those having a variable region derived from a murine mAb and a human immunoglobulin constant region. Antibodies which have variable region framework residues substantially from human antibody (termed an acceptor antibody) and complementarity determining regions substantially from a mouse antibody (termed a donor antibody) are also referred to as humanized antibodies. Chimeric antibodies are primarily used to reduce immunogenicity in application and to increase yields in production, for example, where murine mAbs have higher yields from hybridomas but higher immunogenicity in humans, such that human/murine chimeric mAbs are used. Chimeric antibodies and methods for their production are known in the art (See for example Better et al, 1988; Cabilly et al, 1984; Harlow et al, 1988; Liu et al, 1987; Morrison et al, 1984; Boulianne et al, 1984; Neuberger et al, 1985; Sahagan et al, 1986; Sun et al, 1987; Cabilly et al; European Patent Applications 125023, 171496, 173494, 184187, 173494, PCT patent applications WO 86/01533, WO 97/02671, WO 90/07861, WO 92/22653 and U.S. Pat. Nos. 5,693,762, 5,693,761, 5,585,089, 5,530,101 and 5,225,539). These references are hereby incorporated by reference.

Besides the conventional method of raising antibodies in vivo, antibodies can be generated in vitro using phage display technology. Such a production of recombinant antibodies is much faster compared to conventional antibody production and they can be generated against an enormous number of antigens. In contrast, in the conventional method, many antigens prove to be non-immunogenic or extremely toxic, and therefore cannot be used to generate antibodies in animals. Moreover, affinity maturation (i.e., increasing the affinity and specificity) of recombinant antibodies is very simple and relatively fast. Finally, large numbers of different antibodies against a specific antigen can be generated in one selection procedure. To generate recombinant monoclonal antibodies one can use various methods all based on phage display libraries to generate a large pool of antibodies with different antigen recognition sites. Such a library can be made in several ways: One can generate a synthetic repertoire by cloning synthetic CDR3 regions in a pool of heavy chain germline genes and thus generating a large antibody repertoire, from which recombinant antibody fragments with various specificities can be selected. One can use the lymphocyte pool of humans as starting material for the construction of an antibody library. It is possible to construct naive repertoires of human IgM antibodies and thus create a human library of large diversity. This method has been widely used successfully to select a large number of antibodies against different antigens. Protocols for bacteriophage library construction and selection of recombinant antibodies are provided in the well-known reference text Current Protocols in Immunology, Colligan et al (Eds.), John Wiley & Sons, Inc. (1992-2000), Chapter 17, Section 17.1.

Phage display of human antibody fragments has proved to be an effective method to isolate human antibodies to specific human antigens. In this method, a patient's antibody repertoire is expressed fused to the coat protein of a phage vector that carries the encoded protein gene, with each phage carrying a single antibody specificity. Briefly, antibody V regions are amplified with regions of overlap, either to a separately amplified linker region, or to each other, in such a way that mixing the two V regions recreates a linker region joining the two V genes. A number of amplification cycles without the addition of external primers are first performed. These involve an initial annealing of the regions of overlap followed by an extension. In this way $V_H$ regions are joined to $V_L$ to make the single-chain antibody fragment (scFv) which is, finally, cloned upstream the gene III coding for the minor coat protein g3 in a phagemid vector. Following *E. coli* transformation and infection by a helper phage, phage particles expressing a reactive antibody on their surface are produced. Antibodies specific to a given antigen can be isolated from phage antibody libraries by recursive cycles of binding on an immobilized antigen, washing, elution, and amplification by bacterial infection of bound phages. Finally, bacterial clones expressing single antibody specificity are characterized for the epitope recognized.

Antibodies Against CD55 and CD59 from a Human Phage Display

Cancer cells evade complement-dependent cytotoxicity triggered by humanized antibodies to tumor antigens currently used in cancer therapy, thus limiting the therapeutic potential of these antibodies.

This is due to overexpression of membrane complement regulatory proteins (CRP) including CD55 (decay-accelerating factor (DAF)), that neutralize the activation of C3 convertase, and CD59, that inhibit the polymerization of C9 within the assembling membrane attack complex. Neutralizing murine anti-CRP mAbs have been developed and have been shown to be effective in overcoming the resistance of cancer cells to complement attack as a result of CRPs overexpression. With the introduction of complement-fixing humanized antibodies in cancer therapy, the development of neutralizing humanized or human antibodies may provide an important means to potentiate the therapeutic efficacy of anti-cancer antibodies.

The inventors of the present invention selected neutralizing human antibodies because the humanized antibodies, though less immunogenic than the parental murine antibodies, maintain the murine CDRs coding for non-human V region sequences and may still elicit an antiidiotypic response. The inventors of the present invention have isolated human antibodies to CRPs CD55 and CD59. These antibodies are amenable for development as anticancer therapeutic agents.

An increasing number of mAbs are entering the clinic as therapeutic tools to control tumor growth. The advantage of such Abs over the chemotherapeutic agents is the specificity for the tumoral targets and the recruitment of other soluble or cellular components of the innate immunity to attack cancer cells. The complement (C) system is one of the effector systems called into action by the Abs, but overexpression of CRPs by tumor cells restricts the destructive effect of C. To neutralize the inhibitory activity of CRPs and to potentiate C-mediated killing of B lymphoma cells, the inventors of the present invention have isolated scFv to CD55 and CD59 from a human phage display library to be used alone or in combination with C-fixing Rituximab and other C-activating mAbs. The human phage Abs libraries offer the advantage over conventional mAbs of a large Abs repertoire not shaped by the constraints of the immune system with a dramatic increase in the chances of isolating Abs to self-antigens. On the other hand, the Abs currently used in cancer therapy, unlike human scFv, are of murine origin, and, although engineered to become chimeric or humanized, they still contain murine variable portions of the original Ig that may elicit an antiidiotipic response resulting in their rapid clearance.

As shown in the present invention, the scFvs to CD55 and CD59 were found to be specific for their target antigens and did not cross-react with other CRPs. CD46 was included in the assay as a control antigen because both CD55 and CD46 are members of the same family of proteins named regulators of C activation that share the common domain known as short consensus repeat or C control protein repeat. This family of proteins also includes Factor H, CR1, CR2 and C4 binding protein and is distinct from the Ly-6 multi-gene family, which comprises CD59, urokinase-type plasminogen activator receptor and several other proteins.

The therapeutic use of scFv has so far been limited by the problems encountered in their large-scale production and also by the difficulties in achieving effective and sustained levels at tumour sites. To overcome these problems, the inventors have followed the strategy of engineering a miniantibody (MB), which was produced by genetic fusion of anti-CD55 and anti-CD59 scFv to human IgG1 Hinge-CH2 or to human IgG1 Hinge-CH2 CH3 domains. CH2-CH3 MB were previously found to have increased antigen binding activity and in vivo stability. In the initial screening analysis the scFvs were selected for their ability to neutralize the inhibitory activity of the two CRPs as assessed by the increased C-dependent lysis of erythrocytes expressing these C regulators. It is interesting to note that the two MB derived from the original scFvs inhibited the function of the CRPs to a degree similar to that obtained with well known murine mAbs used as positive controls.

The present invention supports the conclusion that these CRPs play an important role in protecting the tumor cells from C attack and justifies the therapeutic use of the human MB to neutralize their C inhibitory activity thus potentiating the C-mediated destruction of tumors cells induced by C-fixing mAbs.

MB to CD55 and CD59 secreted by cells that were transfected with MB expression vectors were found to be highly effective in reducing the surface expression of the target antigens to about 70 and 80% of the control respectively. The effect obtained in transfected cells raises the possibility of exploiting this strategy to target the tumour cells with immunoliposomes containing MB expression vectors. This may result in the synthesis of intracellular antibodies leading to surface depletion of the CRPs and also in the secretion of MB that neutralize CRPs expressed on the surrounding cells.

The present invention provides two human neutralizing MB to CD55 and CD59 that enhance the C-mediated killing of cancer cells. Co-expression of two MB in the same cell or engineering a bispecific binding molecule may allow the simultaneous abolishment of both CD55 and CD59 on the cell surface.

In another embodiment, the anti CD55 and/or CD59 antibodies according to the present invention are combined with anti CD20 antibodies in a combined composition. This combined composition is advantageous in order to trigger apoptosis in cancer cells overexpressing both CD20 and CD55/CD59. According to this specific embodiment, the combined composition of anti CD55 and/or CD59 antibodies with anti CD20 antibodies comprises either separate antibody molecules directed against the different epitopes, or single bispecific antibody molecules directed against both epitopes. Bispecific antibody molecules are for example quadroma molecules, chemically crosslinked F(ab)$_2$ molecules, single chain bispecific antibody molecules or diabodies.

In a preferred embodiment, the antibody molecules of the present invention are bispecific molecules containing two different antigen-binding regions being operatively attached. The term "operatively attached" is meant attached by covalent or ionic or other linkage. The first antigen-binding region binds to the CD55 or CD59 epitope, and the second antigen-binding region binds to a tumor-specific antigen overexpressed in tumor cells, preferably the CD20 epitope. Without being bound by theory, the combined specificities of the bispecific molecules trigger the immune response to cancer cells overexpressing CD55 and CD59. In one embodiment, the bispecific antibodies are produced by fusing two established hybridoma cell lines to form quadromas (the preparation of quadroma molecules is disclosed for example in Milstein et al., 1983, Nature p. 537-540), or by chemical cross-linking of respective F(ab') fragments (Karpovsky et al., 1984, Exp. Med. 160, p. 1686-1701). Both technologies allowed the production of multiple combinations of antigen specificities.

In another more preferred embodiment, bispecific single-chain Fv fragments may be constructed by combining two single-chain Fv fragments of CD55 or CD59 and CD20 using a polypeptide linker (the preparation of bispecific single-chain Fv fragments is disclosed for example in Mack et al., 1995, Proc. Natl. Acad. Sci., 92 p. 7021-7025). These constructs are expressed as single covalently linked molecules, showing high thermal stability at 37° C. Thus single-chain Fv fragments derived from monoclonal antibodies against CD55 or CD59 are covalently linked with single-chain Fvs directed against CD20 to produce the bispecific single-chain Fv fragments.

In another preferred embodiment, the dual specificity is obtained with diabodies that are non-covalently associated dimers, in which each chain comprises two domains consisting of VH (variable heavy) and VL (variable light) domains from two different antibodies (Holliger et al., 1993, Proc. Natl. Acad. Sci., 90, p. 6444-6448). Both domains are connected by a linker which is too short to allow pairing between domains of the same chain. Thus, each chain alone is not capable of binding antigen, but co-expression of the two chains ($V_H$CD55/59-$V_L$CD20 and $V_H$CD20-$V_L$CD55/59) leads to assembly of heterodimeric bispecific diabodies. In contrast to IgG or F(ab)$_2$, the diabody structure is more compact, with the two binding sites separated by only 6.5 nm (less than half the distance present in IgG), and with a typical molecular mass of only approx. 50 kDa. Owing to this small size, diabodies are expected to show rapid pharmacokinetics and improved tumor penetration in vivo.

In a more specific embodiment, the dual specificity is obtained with heterodimeric diabodies having two separate arms as follows. The first arm comprises a single-chain Fv fragment of CD55/59 (VH and VL domains) preferably covalently linked with human CH2 and CH3 constant domains. The second arm comprises a single-chain Fv fragment of CD20 (VH and VL domains) preferably covalently linked with human CH2 and CH3 constant domains. The inclusion of CH2 and CH3 constant domains allows the activation of antibody-dependent cellular cytotoxicity (ADCC). In this context, one arm of the heterodimeric diabody binds the CD20 antigen on the tumor cell, and the other arm binds the CD55/59 antigen overexpressed in the tumor cells.

The bispecific antibody molecules according to the present invention may be produced using methods known in the art such as hybrid hybridomas, DNA co-transfection and chemical conjugation. A major obstacle in the development of bispecific antibody molecules has been the difficulty of producing proper heterodimers with two different arms and in sufficient quantity for clinical application by the traditional methods. Hybrid hybridomas and DNA co-transfection give rise to a large number of undesired products which require a purification of the desired products from the other products. Another traditional method for heterodimeric diabodies production is chemical conjugation of two antibodies (or their fragments) of different specificities. The purification from undesired products leads to a low yield and poor quality of heterodimeric diabodies. Preferred method for heterodimeric diabodies production is the "knob into holes" method first developed by Carter et al (Ridgway, J. B., Presta, L. G., Carter, P., 1996. "Knobs-into-holes" engineering of antibody CH3 domains for heavy chain heterodimerization. Protein Eng. 9, 617). The "Knobs-into-holes" method favours the production of heterodimers over homodimers and is based on the idea that simple mutations can be introduced into one half of the CH3 dimer, such that the steric complementarity required for CH3/CH3 association obligates the mutated CH3 domain to pair with a CH3 domain that has different, accommodating mutations. In a preferred embodiment, a mutation designated as a "knob" mutation is obtained by replacing a small amino acid residue (e.g. threonine) with a large amino acid residue (e.g. tyrosine) in the CH3 domain of the first minibody (the CD20 minibody). This mutation creates a steric barrier to homodimerization. To promote heterodimerization, an accommodating mutation designated as a "hole" mutation is obtained by replacing a large amino acid residue (e.g. tyrosine) with a small amino acid residue (e.g. threonine) in the CH3 domain of the second minibody (the CD55/CD59 minibody). In a non-limiting example of the present invention, threonine-26 residue is replaced with tyrosine in the CD20 minibody, and tyrosine-67 is replaced with threonine in the CD55/59 minibody.

Recombinant bispecific antibodies can be successfully produced in various expression systems. Production in *Escherichia coli* is most commonly used for the diabody format (see for example Xiong et al., 2002, Cancer Lett. 177, p. 29-39). Short-chain bispecific antibodies are preferentially expressed in mammalian cells such as CHO or COS cells (Wuest et al., 2001, J. Biotechnol. 92, 159-168). Other possible expression systems include yeast or insect cells, as well as transgenic plants or animals (Verma et al., 1998, Immunol. Methods, 216, p. 165-181; Gavilondo et al., 2000, Biotechniques 29, p. 128-132). Purification of recombinant bispecific antibodies can be achieved by methods known in the art, for example by one or more of several well-defined affinity tags, such as poly-histidine or strep (Skerra et al., 2000, Methods Enzymol. 326, p. 271-304).

In another embodiment, the antibody molecules of the present invention are, trispecific antibody molecules containing three different binding specificities: the first binding specificity is directed against a CD55 epitope, the second binding specificity is directed against a CD20 epitope, and the third binding specificity is directed against a CD59 epitope.

The trimeric specificity is obtained with heterodimeric minibody having two separate arms as suggested for example in Shahied et al. (Shahied L S, Tang Y, Alpaugh R K, Somer R, Greenspon D, Weiner L M. Bispecific minibodies targeting HER2/neu and CD16 exhibit improved tumor lysis when placed in a divalent tumor antigen binding format. J Biol Chem. 2004 Dec. 24; 279(52):53907-14.)

According to a preferred embodiment, the first arm of the heterodimeric minibody comprises a single-chain Fv fragment to CD55 (VH and VL domains) operatively attached, preferably covalently attached with human CH2 and CH3 constant domains. The second arm comprises a single-chain Fv fragment to CD20 (VH and VL domains) operatively attached, preferably covalently attached with human CH2 and CH3 constant domains. The second arm contains at the C-terminal end of the CH3 a linker peptide followed by the third single chain Fv fragment to CD59 (VH and VL domains). The linker is in the length of between 10 to 40 amino acid residues, preferably between 20 to 30 amino acid residues, most preferably between 20 to 25 amino acids residues. The relative position of the scFv to CD55 and CD59 in the different arms of the molecule may be inverted. The trispecific antibodies could be produced using specific expression vectors known in the art such as the vector described herein in the Examples.

Preferred Embodiments

One aspect of the present invention is directed to neutralizing antibodies and more generally to a molecule that comprises one or more of the CDR3 variable regions of SEQ ID NO: 14, 16, 18, 20 of a recombinant antibody which binds to CD55 and/or CD59. The antibodies may be encoded by polynucleotides (DNA) having SEQ ID NO:13, 15, 17, 19 respectively.

The molecule having the CDR3 variable regions of an antibody according to the present invention can be used in a method for modulating complement activation. A preferred embodiment of such antibodies/molecules, obtained from a phage display of human antibody library, are the specific clones with the unique $V_H$ CDR3 and $V_L$. CDR3 sequences given in Table 1.

TABLE 1

| | V family | V gene | CDR3 amino acid sequence | CDR3 nucleotide sequence |
|---|---|---|---|---|
| ANTI CD55 VL | VL3 | DPL16 | SSRDNRGTHRWV SEQ ID NO: 14 | cgggacaacagaggtacccatcgatgggtc SEQ ID NO: 13 |
| ANTI CD55 VH | VH3 | DP31 | DRSDRGRLLDY SEQ ID NO: 16 | gataggtccgatcgtggcagactccttgactac SEQ ID NO: 15 |
| ANTI CD59 VL | VK IV | DPK24 | QQYYSTPQLT SEQ ID NO: 18 | cagcaatattatagtactcctcagctca ct SEQ ID NO: 17 |
| ANTI CD59 VH | VH3 | VH3-48 | GPGMDV SEQ ID NO: 20 | gggcctggtatggacgtc SEQ ID NO: 19 |

The two scFv, further developed in minibodies by adding CH2 and CH3 human antibody domains. The two scFv show unique characteristics and their encoding nucleotide sequences (both total and partial) are novel. The main features are:

A. Sequence
1. Unique $V_H/V_L$ cDNA sequence due to: a. CDR3 specific rearrangement.
B. Reactivity
1. Very good inhibitory properties of the biological functions of CD55 and CD59.
C. Engineering
1. Suitable for further modification by adding human or animal antibody constant domains. The antibody maintains its reactivity.
2. Expression in vertebrate cells. The antibody is well expressed and functional in vivo when subcloned in a eukaryotic vector.

The nucleotide sequences of the $V_L$, linker and $V_H$ domains of the preferred embodiment of the present invention are presented below.

```
Clone anti CD 59
V_L-nucleotide sequence (SEQ ID NO: 1):
GATATTGTGTTGACACAGTCTCCAGACTCCCTGGCTGTGTCTCTGGGCGAGAGGGCCACCAT

CAACTGCAAGTCCAGCGAGAGTGTTTTATACAGCTCCAACAATAAGAACTACTTAGCTTGGT
```

-continued

ACCAGCAGAAACCAGGACAGCCTCCTAAGCTGCTCATTTACTGGGCATCTACCCGGGAATCC

GGGGTCCCCGACCGATTCAGTGGCAGCGGGTCTGGGACAGATTTCACTCCCGCCATCAGCAG

CCTGCAGGCTGAAGATGTGGCAGTTTATTACTGTCAGCAATATTATAGTACTCCTCAGCTCA

CTTTCGGCGGAGGGACCAAAGTGGATATCAAA $V_L$-corresponding amino acid sequence (SEQ ID NO: 2):
DIVLTQSPDSLAVSLGERATINCKSSQSVLYSSNNKNYLAWYQQKPGQPPKLLIYWASTRESGVP

DRFSGSGSGTDFTPAISSLQAEDVAVYYCQQYYSTPQLTFGGGTKVDIK

Linker-nucleotide sequence (SEQ ID NO: 3):
TCCGGAGGGTCGACCATAACTTCGTATAATGTATACTATACGAAGTTATCCTCGAGCGGTAC

C

Linker - corresponding amino-acid sequence of (SEQ ID NO: 4):
SGGSTITSYNVYYTKLSSSGT $V_H$ nucleotide sequence (SEQ ID NO: 5):
CAGGTACAGCTGCAGCAGTCAGGGGGAGGCGTGGTCCAGCCTGGGAGGTCCCTGGGACTCT

CCTGTGCAGCGTCTGGATTCACCTTCAGTAGCTATGGCATGAACTGGGTCCGCCAGGCTCCA

GGGAAGGGGCTGGAGTGGGTTTCATACATTAGTAGTAGTAGTAGTACCATATACTACGCAG

ACTCTGTGAAGGGCCGATTCACCATCTCCAGAGACAATTCCAAGAACACGCTGTATCTGCAA

ATGAACAGCCTGAGAGCCGAGGACACGGCTGTGTATTACTGTGCGAGAGGGCCTGGTATGG

ACGTCTGGCGCCAAGGGACAACGGTCACCGTCTCTTCA $V_H$-corresponding amino acid sequence (SEQ ID NO: 6):
QVQLQQSGGGVVQPGRSLGLSCAASFTFSSYGMNWVRQAPGKGLEWVSYISSSSSTIYADSV

KGRFTISRDNSKNTLYLQMNSLRAEDTAVYYCARGPGMDVWGQGTTVTVS

Clone anti CD 55
$V_L$-nucleotide sequence (SEQ ID NO: 7):
TCGTCTGAGCTGACTCAGGAGCCTGCTGTGTCTGTGGCCTTGGGACAGACAGTCTCGATCAC

GTGCCAAGGAGACAGCCTCAGAAGCTATTATGCAAGCTGGTACCAACAGAAGCCAGGACAG

GCCCCTATTCCTGTCATTTATGGTAAAAATAACCGGCCCTCAGGGATCCCAGACCGATTCTCT

GGCTCCAGCTCAGGAAACACAGCTTCGTTGACCATCACTGGGGCTCAGGCGGAAGATGAGG

CTGACTATTACTGTAGCTCCCGGGACAACAGAGGTACCCATCGATGGGTCTTCGGCGGAGGG

ACCAAGCTCACCGTCCTA $V_L$-corresponding amino acid sequence (SEQ ID NO: 8):
SSELTQEPAVSVALGQTVSITCQGDSLRSYYASWYQQKPGQAPIPVIYGKNNRPSGIPDRFSGSSS

GNTASLTITGAQAEDEADYYCSSRDNRGTHRWVFGGGTKLTVL

Linker-nucleotide sequence (SEQ ID NO: 9):
TCCGGAGGGTGGACCATAACTTCGTATAATGTATACTATACGAAGTTATCCTCGAGCGGTAC

C

Linker - corresponding amino-acid sequence of (SEQ ID NO: 10):
SGGSTITSYNVYYTKLSSSGT $V_H$ nucleotide sequence (SEQ ID NO: 11):
CAGGTCAACTTAAGGGAGTCTGGGGGAGGCTTGGTACAGCCTGGCAGGTCCCTGAGACTCTC

CTGTGCAGCCTCTGGATTCACCTTTGATGATTATGCCATGCACTGGGTCCGGCAAGCTCCAG

GGAAGGGCCTGGAGTGGGTCTCAGGTATTAGTTGGAATAGTGGTAGCATAGGCTATGCGGA

CTCTGTGAAGGGCCGATTTACCATCTCCAGAGACAACGCCAAGAACTCCCTGTATCTGCAAA

```
                                -continued
TGAACAGTCTGAGAGCTGAGGACACGGCCTTGTATTACTGTGCAAAAGATAGGTCCGATCGT

GGCAGACTCCTTGACTACTGGGGCCTGGGAACCCTGGTCACCGTCTCCTCA

V_H -corresponding amino acid sequence (SEQ ID NO: 12):
QVNLRESGGGLVQPGRSLRLSCAASGFTFDDYAMHWVRQAPGKGLEWVSGISWNSGSIGYADS

VKGRFTISRDNAKNSLYLQMNSLRAEDTALYYCAKDRSDRGRLLDYWGLGTLVTVS
```

The antibodies of the invention are preferably of human origin, i.e. they are entirely derived from an antibody repertoire obtained from human serum. These antibodies have both framework and antigen complementary regions (CDR) of human origin, unlike humanized antibodies where only the framework is of human origin, while the CDR are of murine origin.

In one embodiment, the recombinant antibody of the invention comprises a $V_L$ chain consisting of a sequence preferably corresponding to SEQ ID NO: 2 or 8 that could be covalently linked to a $V_H$ chain preferably corresponding to SEQ ID NO: 6 or 12, respectively. In another embodiment, the recombinant antibody comprises one or more of the amino acid sequences of SEQ ID NO: 2, 6, 8 or 12. In a preferred embodiment, the recombinant antibody comprises a $V_L$ and $V_H$ region consisting of SEQ ID NO: 2 and 6 and a linker consisting of SEQ ID NO: 4 respectively. In another preferred embodiment, the recombinant antibody comprises a $V_L$ and $V_H$ region consisting of SEQ ID NO: 8 and 12 and a linker consisting of SEQ ID NO: 10 respectively.

In another aspect, the present invention provides pharmaceutical compositions comprising the antibody molecules. The pharmaceutical compositions according to the present invention are similar to those used for passive immunization of humans with other antibodies. Typically, the antibody molecules of the present invention comprising the antigen binding portion of an antibody are suspended in a sterile saline solution for therapeutic uses. The pharmaceutical compositions may alternatively be formulated to control release of active ingredient (molecule comprising the antigen binding portion of an antibody) or to prolong its presence in a patient's system. Numerous suitable drug delivery systems are known and include, e.g., implantable drug release systems, hydrogels, hydroxymethylcellulose, microcapsules, liposomes, microemulsions, microspheres, and the like. Controlled release preparations can be prepared through the use of polymers to complex or adsorb the molecule according to the present invention. For example, biocompatible polymers include matrices of poly (ethylene-co-vinyl acetate) and matrices of a polyanhydride copolymer of a stearic acid dimer and sebaric acid. The rate of release of the molecule according to the present invention, i.e., of an antibody or antibody fragment, from such a matrix depends upon the molecular weight of the molecule, the amount of the molecule within the matrix, and the size of dispersed particles.

The pharmaceutical composition of this invention may be administered by any suitable means, such as orally, intranasally, subcutaneously, intramuscularly, intravenously, intraarterially, intralesionally, rectally, vaginally or intraperitoneally. Ordinarily, intravenous (i.v.) or intramuscular administration is preferred.

It will be apparent to those of ordinary skill in the art that the therapeutically effective dose of the molecule according to the present invention will depend, inter alia upon the administration schedule, the unit dose of molecule administered, whether the molecule is administered in combination with other therapeutic agents, the immune status and health of the patient, the therapeutic activity of the molecule administered and the judgment of the treating physician. As used herein, a "therapeutically effective dose" refers to the dose of a molecule required to alleviate one or more symptoms associated with a disorder being treated over a period of time.

Although an appropriate dosage of a molecule of the invention varies depending on the administration route, age, body weight, sex, or conditions of the patient, and should be determined by the physician in the end, in the case of oral administration, the daily dosage can generally be between about 0.01-200 mg, preferably about 0.01-10 mg, more preferably about 0.1-10 mg, per kg body weight. In the case of parenteral administration, the daily dosage can generally be between about 0.001-100 mg, preferably about 0.001-1 mg, more preferably about 0.01-1 mg, per kg body weight The daily dosage can be administered, for example in regimens typical of 1-4 individual administration daily. Various considerations in arriving at an effective amount are described, e.g., in Goodman and Gilman's: The Pharmacological Bases of Therapeutics, 8th ed., Pergamon Press, 1990; and Remington's Pharmaceutical Sciences, 17th ed., Mack Publishing Co., Easton, Pa., 1990.

The antibody molecule of the present invention as an active ingredient is dissolved, dispersed or admixed in an excipient that is pharmaceutically acceptable and compatible with the active ingredient as is well known. Suitable excipients are, for example, water, saline, phosphate buffered saline (PBS), dextrose, glycerol, ethanol, or the like and combinations thereof. Other suitable carriers are well-known to those in the art. In addition, if desired, the composition can contain minor amounts of auxiliary substances such as wetting or emulsifying agents, pH buffering agents.

The antibody molecules of the invention may be administered alone or in combination with one or more further agents. Thus, the present invention further provides products comprising molecules that bind to CD55 and/or CD59 and an active agent as a combined preparation for simultaneous, separate or sequential use in the treatment of cancer. Active agents may include antibodies directed against, tumor-specific antigens, preferably antibodies directed against tumor-specific antigens overexpressed in B cells such as an anti-CD20 antibody e. g Rituxan (Rituximab) (Biogen IDEC (Cambridge, Mass., USA); an anti-VEGF antibody e. g. Avastin (bevacizumab), Genentech (South San Francisco, Calif., USA)/(Roche (Basel, Switzerland); an anti-CD171A antibody, e. g. Panorex (edrecolomab) Centocor (Malvern, Pa., USA)/Glaxo SmithKline (Uxbridge, UK); an anti-CEA anti-idiotypic mAb e.g. CeaVac, Titan Pharmaceuticals (South San Francisco, Calif., USA); an anti-EGFR antibody e.g. Erbitux (cetuximab), ImClone (New York, USA)/Bristol Myers Squibb (New York, USA), Merck (Whitehouse Station, N.J., USA); an anti-HMFG anti-idiotypic mAb e. g TriAb, Titan Pharmaceuticals (South San Francisco, Calif., USA), an anti-EGFR antibody e.g. ABX-EGF, Abgenix (Fremont, Calif., USA)/Amgen Thousand Oaks, Calif.) and/or an anti-HER2 antibody e.g. Herceptin, Genentech (South San Francisco, Calif., USA). Preferably, the active agent synergizes with the antibody molecule of the invention. Without being bound by theory, the ability of the molecule of the invention to synergize with an active agent to enhance tumor killing may not be due to immune effector mechanisms but rather may be a direct consequence of inactivating CD55 and/or CD59 allowing enhanced complement deposition and complement lysis.

An "antibody directed against tumor-specific antigens overexpressed in B cells" herein is an antibody specific for a marker expressed on the surface of a B cell. Exemplary B cell surface markers include the CD10, CD19, CD20, CD21, CD22, CD23, CD24, CD37, CD53, CD72, CD73, CD74, CDw75, CDw76, CD77, CDw78, CD79a, CD79b, CD80, CD81, CD82, CD83, CDw84, CD85 and CD86 leukocyte surface markers. The B cell surface marker of particular interest is preferentially expressed on B cells compared to other non-B cell tissues of a mammal and may be expressed on both precursor B cells and mature B cells. In one embodiment, the marker is one, like CD20 or CD19, which is found on B cells throughout differentiation of the lineage from the stem cell stage up to a point just prior to terminal differentiation into plasma cells. The preferred B cell surface markers herein are CD19 and CD20.

As used herein, the term "anti-CD20 antibody" is an antibody which specifically recognizes a cell surface non-glycosylated phosphoprotein of 35,000 Daltons, typically designated as the human B lymphocyte restricted differentiation antigen Bp35, commonly referred to as CD20.

Examples of antibodies which bind the CD20 antigen include: "C2B8" which is now called "Rituximab" (U.S. Pat. No. 5,736,137, expressly incorporated herein by reference); the yttrium-[90]-labeled 2138 murine antibody designated "Y2B8" (U.S. Pat. No. 5,736,137, expressly incorporated herein by reference); murine IgG2a "131" optionally labeled with 131I to generate the "131I-B1" antibody (U.S. Pat. No. 5,595,721, expressly incorporated herein by reference); murine monoclonal antibody "1F5" (Press et al. Blood 69(2): 584-591 (1987)); "chimeric 2H7" antibody (U.S. Pat. No. 5,677,180, expressly incorporated herein by reference); and monoclonal antibodies L27, G28-2, 93-1133, B-C1 or NU-B2 available from the International Leukocyte Typing Workshop (Valentine et al., In: Leukocyte Typing III (McMichael, Ed., p. 440, Oxford University Press (1987)).

Examples of antibodies which bind the CD19 antigen include the anti-CD19 antibodies in Hekman et al., Cancer Immunol. Immunother. 32:364-372 (1991) and Vlasveld et al. Cancer Immunol. Immunother. 40:37-47 (1995); and the B4 antibody in Kiesel et al. Leukemia Research 11, 12: 1119 (1987).

The terms "Rituximab" herein refer to the genetically engineered chimeric murine/human mono clonal antibody directed against the CD20 antigen and designated "C2B8" in U.S. Pat. No. 5,736,137, expressly incorporated herein by reference. The antibody is an IgG, kappa immunoglobulin containing murine light and heavy chain variable region sequences and human constant region sequences. Rituximab has a binding affinity for the CD20 antigen of approximately 8.0 nM.

In another embodiment, the antibody molecules of the invention may be administered in combination with at least one cytokine, wherein the therapeutic effect is better than the additive effects of either therapy administered alone. Preferred cytokines are selected from the group consisting of alpha interferon, gamma interferon, IL-2, GM-CSF and G-CSF. Again, the anti-CD-55/59 antibody and the cytokine(s) may be administered sequentially, in either order, or in combination.

In another embodiment, the antibody molecules of the invention may be administered before, during or subsequent to a chemotherapeutic treatment or combination regimens. Such chemotherapeutic treatments may be for example: CHOP (cyclophosphamide, Oncovin, prednisone and doxorubicin), ICE (Ifosfamide, Carboplatin, Etoposide), Mitozantrone, Cytarabine, DVP (Daunorubicin, Vincristine Prednisolone), Idarubicin, ABVD (Adriamycin, bleomycin, vinblastine, dacarbazine), CEOP (Cyclophosphamide Epirubicin, oncovin, Prednisolone), 2-CdA (2-Chlorodeoxyadenosine), and DHAP (Dexamethasone, High dose Ara-C (Cytarabine), Cisplatin (platinum)).

Other chemotherapeutic treatment that may be used in combination with the present invention are for example: etoposide, 5-FU (5-fluorouracil), cis-platinum, doxorubicin, a vinca alkaloid, vincristine, vinblastine, vinorelbine, taxol, cyclophosphamide, ifosfamide, chlorambucil, busulfan, mechlorethamine, mitomycin, dacarbazine, carboplatinum, thiotepa, daunorubicin, idarubicin, mitoxantrone, bleomycin, esperamicin A1, dactinomycin, plicamycin, carmustine, lomustine, tauromustine, streptozocin, melphalan, dactinomycin, procarbazine, dexamethasone, prednisone, 2-chlorodeoxyadenosine, cytarabine, docetaxel, fludarabine, gemcitabine, herceptin, hydroxyurea, irinotecan, methotrexate, oxaliplatin, rituxin, semustine, epirubicin, etoposide, tomudex and topotecan, or a chemical analog of one of these chemotherapeutic agents.

"Treatment of cancer" includes treatment of conditions caused by cancerous growth and includes the treatment of neoplastic growth or tumors. Examples of tumors that can be treated by the molecule of the invention are, for instance, sarcomas, including osteogenic and soft tissue sarcomas, carcinomas, e.g., breast-, lung-, bladder-, thyroid-, prostate-, colon-, rectum-, pancreas-, stomach-, liver-, uterine-, cervical and ovarian carcinoma, lymphomas, including Hodgkin and non-Hodgkin lymphomas, neuroblastoma, melanoma, myeloma, Wilms tumor, and leukemias, including acute lymphoblastic leukaemia and acute myeloblastic leukaemia, gliomas and retinoblastomas. The antibody molecules of the invention may, upon binding to CD55 and/or CD59 present on cancerous cells or tissues, including tumor and non-tumor cells, neutralize CD55 and/or CD59 and enhance complement deposition and complement mediated lysis of these cells. The compositions and methods of the invention may be particularly useful in the treatment of existing cancer and in the prevention of the recurrence of cancer after initial treatment or surgery.

When combined with anti CD20 antibodies, the antibody molecules of the present invention may be used to treat a range of cancers as described above, in particular to treat a variety of B-cell lymphomas, including low grade/follicular non-Hodgkin's lymphoma (NHL), small lymphocytic (SL) NHL, intermediate grade/follicular NHL, intermediate grade diffuse NHL, high grade inimunoblastic NHL, high grade lymphoblastic NHL, high grade small non-cleaved cell NHL, bulky disease NHL and Waldenstrom's Macroglobulinemia.

The present invention also provides for a nucleic acid molecule, which contains a nucleotide sequence encoding the molecule having the antigen binding portion of an antibody that neutralizes CD55 and/or CD59 and a host cell transformed with this nucleic acid molecule. Furthermore, also within the scope of the present invention is a nucleic acid molecule containing a nucleotide sequence having at least 90% sequence identity, preferably about 95%, and more preferably about 97% identity to the above encoding nucleotide sequence as would well understood by those of skill in the art.

The invention also provides nucleic acids that hybridize under high stringency conditions to polynucleotides having SEQ ID NO: 1, 5, 7 and 11 or the complement thereof. As used herein, highly stringent conditions are those which are tolerant of up to about 5-20% sequence divergence, preferably about 5-10%. Without limitation, examples of highly stringent (-10° C. below the calculated Tm of the hybrid) conditions use a wash solution of 0.1×SSC (standard saline citrate) and 0.5% SDS at the appropriate Ti below the calculated Tm of the hybrid. The ultimate stringency of the conditions is primarily due to the washing conditions, particularly if the hybridization conditions used are those which allow less stable hybrids to form along with stable hybrids. The wash conditions at higher stringency then remove the less stable hybrids. A common hybridization condition that can be used with the highly stringent to moderately stringent wash conditions described above is hybridization in a solution of 6×SSC (or 6×SSPE), 5×Denhardt's reagent, 0.5% SDS, 100 µg/ml denatured, fragmented salmon sperm DNA at an appropriate incubation temperature Ti. See generally Sambrook et al., Molecular Cloning: A Laboratory Manual, 2d edition, Cold Spring Harbor Press (1989) for suitable high stringency conditions.

Stringency conditions are a function of the temperature used in the hybridization experiment and washes, the molarity of the monovalent cations in the hybridization solution and in the wash solution(s) and the percentage of formamide in the hybridization solution. In general, sensitivity by hybridization with a probe is affected by the amount and specific activity of the probe, the amount of the target nucleic acid, the detectability of the label, the rate of hybridization, and the duration of the hybridization. The hybridization rate is maximized at a Ti (incubation temperature) of 20-25° C. below Tm for DNA:DNA hybrids and 10-15° C. below Tm for DNA:RNA hybrids. It is also maximized by an ionic strength of about 1.5M Na$^+$. The rate is directly proportional to duplex length and inversely proportional to the degree of mismatching.

Specificity in hybridization, however, is a function of the difference in stability between the desired hybrid and "background" hybrids. Hybrid stability is a function of duplex length, base composition, ionic strength, mismatching, and destabilizing agents (if any).

The Tm of a perfect hybrid may be estimated for DNA:DNA hybrids using the equation of Meinkoth et al (1984), as $$Tm=81.5°\,C.+16.6(\log M)+0.41(\%\,GC)-0.61(\%\,form)-500/L$$

and for DNA:RNA hybrids, as $$Tm=79.8°\,C.+18.5(\log M)+0.58(\%\,GC)-11.8(\%\,GC)^2-0.56(\%\,form)-820/L$$

where
M, molarity of monovalent cations, 0.01-0.4 M NaCl,
% GC, percentage of G and C nucleotides in DNA, 30%-75%,
% form, percentage formamide in hybridization solution, and
L, length hybrid in base pairs.

Tm is reduced by 0.5-1.5° C. (an average of 1° C. can be used for ease of calculation) for each 1% mismatching.

The Tm may also be determined experimentally. As increasing length of the hybrid (L) in the above equations increases the Tm and enhances stability, the full-length rat gene sequence can be used as the probe.

Filter hybridization is typically carried out at 68° C., and at high ionic strength (e.g., 5-6×SSC), which is non-stringent, and followed by one or more washes of increasing stringency, the last one being of the ultimately desired high stringency. The equations for Tm can be used to estimate the appropriate Ti for the final wash, or the Tm of the perfect duplex can be determined experimentally and Ti then adjusted accordingly.

The present invention also relates to a vector comprising the nucleic acid molecule of the present invention. The vector of the present invention may be, e.g., a plasmid, cosmid, virus, bacteriophage or another vector used e.g. conventionally in genetic engineering, and may comprise further genes such as marker genes which allow for the selection of the vector in a suitable host cell and under suitable conditions.

Furthermore, the vector of the present invention may, in addition to the nucleic acid sequences of the invention, comprise expression control elements, allowing proper expression of the coding regions in suitable hosts. Such control elements are known to the artisan and may include a promoter, a splice cassette, translation initiation codon, translation and insertion site for introducing an insert into the vector.

Preferably, the nucleic acid molecule of the invention is operatively attached to the above expression control sequences allowing expression in eukaryotic or prokaryotic cells. Control elements ensuring expression in eukaryotic or prokaryotic cells are well known to those skilled in the art. As mentioned herein above, they usually comprise regulatory sequences ensuring initiation of transcription and optionally poly-A signals ensuring termination of transcription and stabilization of the transcript.

Methods for construction of nucleic acid molecules according to the present invention, for construction of vectors comprising the above nucleic acid molecules, for introduction of the vectors into appropriately chosen host cells, for causing or achieving the expression are well-known in the art (see, e.g., Sambrook et al., 1989; Ausubel et al., 1994).

The invention also provides for conservative amino acid variants of the molecules of the invention. Variants according to the invention also may be made that conserve the overall molecular structure of the encoded proteins. Given the properties of the individual amino acids comprising the disclosed protein products, some rational substitutions will be recognized by the skilled worker. Amino acid substitutions, i.e. "conservative substitutions," may be made, for instance, on the basis of similarity in polarity, charge, solubility, hydrophobicity, hydrophilicity, and/or the amphipathic nature of the residues involved.

For example: (a) nonpolar (hydrophobic) amino acids include alanine, leucine, isoleucine, valine, proline, phenylalanine, tryptophan, and methionine; (b) polar neutral amino acids include glycine, serine, threonine, cysteine, tyrosine, asparagine, and glutamine; (c) positively charged (basic) amino acids include arginine, lysine, and histidine; and (d) negatively charged (acidic) amino acids include aspartic acid and glutamic acid. Substitutions typically may be made within groups (a)-(d). In addition, glycine and proline may be substituted for one another based on their ability to disrupt α-helices. Similarly, certain amino acids, such as alanine, cysteine, leucine, methionine, glutamic acid, glutamine, histidine and lysine are more commonly found in α helices, while valine, isoleucine, phenylalanine, tyrosine, tryptophan and threonine are more commonly found in β-pleated sheets. Glycine, serine, aspartic acid, asparagine, and proline are commonly found in turns. Some preferred substitutions may be made among the following groups: (i) S and T; (ii) P and G; and (iii) A, V, L and 1. Given the known genetic code, and recombinant and synthetic DNA techniques, the skilled scientist readily can construct DNAs encoding the conservative amino acid variants.

As used herein, "sequence identity" between two polypeptide sequences indicates the percentage of amino acids that are identical between the sequences. "Sequence similarity"

indicates the percentage of amino acids that either are identical or that represent conservative amino acid substitutions.

Having now generally described the invention, the same will be more readily understood through reference to the following examples, which are provided by way of illustration and are not intended to be limiting of the present invention.

EXAMPLES

Materials and Methods
(i) Antibodies. The anti-CD20 chimeric mAb Rituximab was kindly provided by Dr. Josèe Golay (Milan, Italy). The mAb GB24 to CD46 and mAb YTH53.1 to CD59 were kind gifts from Prof. John P. Atkinson (St Louis, USA) and Prof. Seppo Meri (Helsinki, FINLAND) respectively. The mAb BRIC216 to CD55 was purchased from Serotec (Oxford, United Kingdom). Control IgG were purified from rat and mouse serum by affinity chromatography on HiTrap Protein G column (Pharmacia, Milan, Italy) following published procedure (Langeggen et al., 2000, Clin Exp Immunol, 121: 69-76). All the secondary antibodies to human, mouse and rat Ig were purchased from Sigma-Aldrich (Milan, Italy).
(ii) Antigens. CD55 and CD59 were purified from 150 ml of packed human erythrocytes and CD46 from the buffy coat derived from 1 unit of blood, both provided from the Blood Transfusion Center, Trieste, Italy. The red cells and leukocytes were washed extensively in PBS and incubated with PBS containing 100 mM non-ionic detergent n-octil-glucopyranoside (Sigma-Aldrich) for 30 min at 4° C. After removal of the insoluble material by centrifugation, the supernatants from the two preparations were loaded on a Mono Q column (Pharmacia Biotech, Milan, Italy) equilibrated with PBS and the bound proteins were eluted with a linear gradient of 0-1M NaCl in PBS. The fractions were examined for the presence of CD46, CD55, and CD59 by dot spot analysis using mAb GB24, BRIC216, and YTH53.1 followed by alkaline phosphatase labelled secondary antibody. The fractions containing the highest amount of the three CRPs were pooled and the purity of the preparations checked by SDS-PAGE on a 10% gel under nonreducing conditions was found to be higher than 90%.
(iii) B lymphoma cell lines. Bjab and Karpas lymphoma cell lines were kindly provided by Dr. Josèe Golay (Milan, Italy). Six spontaneous lymphoma cell lines were obtained through the courtesy of Prof. A. Amadori (Padova, Italy) (Piovan et al., 2003, Leukemia, 17: 1643-1649). All these cell lines were cultured in RPMI 1640 medium (Sigma) supplemented with 10% foetal calf serum (Gibco, Invitrogen, Milan, Italy).
(iv) Bacterial strains and enzymes. DH5αF' (F'/endA1 hsdR17($r^K$ $m^{K+}$) supE44 thi-1 recA1 gyrA (Nal$^r$) relA1 D (lacZYA-argF) U169 deoR (F80dlacD(lacZ)M15) strain was used for the cloning of pDAN5, PUT-SEC and derivates, pCDNA3. Molecular biology enzymes were purchased from New England Biolabs (Milan, Italy), Promega (Milan, Italy) or Life Technologies (Invitrogen, Milan, Italy).
(v) Selection of phagemid library and panning. The Abs library used for selection was derived from peripheral blood lymphocytes obtained from healthy donors and was previously described in detail (Sblattero et al., 2000, Nat Biotechnol 18: 75-80). Panning was performed in immunotubes (Nunc, Mascia Brunelli, Milan, Italy) coated with purified CD55 and CD59(10 µg/ml) in 0.1 M sodium bicarbonate buffer pH 9.6 by overnight incubation at 4° C. as previously reported (Marzari et al., 2002, Eur J Immunol. 32: 2773-2782). The panning procedure was repeated twice and the phages from single colonies were grown in 96-well plates.
(vi) Fingerprinting and sequencing of the clones. The V genes of positive clones for each protein were amplified by PCR using V gene primers as described (Sblattero & Bradbury, 1998, Immunotechnology, 3: 271-278).

The V genes from the different anti-CD55 and anti-CD59 clones were sequenced, and the VH and VL families as well as the gene segments used were assessed by screening against the VBASE database.
(vii) Miniantibody cloning. PUT-SEC (Li et al., 1997, Protein Eng. 10: 731-736). The plasmid vector was modified as follows: BspEI site was exchanged with BssHII by inverse polymerase chain reaction (PCR) using the primers PUT-ApaLI ATCCGAGTGCACACCTGTGGAGAGAAAGGCAAAG (SEQ ID NO: 21)
and PUT-BssHII TCCTCAGCGCGCGGCTCTGGTGGCAGACCGAAGG (SEQ ID NO: 22). The human IgG1 CH2 human gene was amplified by PCR with the primers HuGCH2-s AGGCG GCGCGCGACAAAACTCACACATGCCCACCGTGCCCA (SEQ ID NO: 23) and HuGCH3-a ACGTCGATCGCCTGCT GAATTCTTAAGTACTATCCAGGCCCAGCAGTGGGTTTGGGATTGGT TTGCC ACTAGTTTTACCCGGGGACAGGGAGAG (SEQ ED NO:24) which introduces the SV5 tag sequence for mAb SV5 recognition (Hanke et al., 1992, J Gen Virol. 73(Pt 3):653-660) and SpeI, EcoRI and PvuI sites at the 3' end. CH2 PCR fragment was cloned as BssHII-Pvu 1 in the PUT-SEC vector. The cloning of individual scFv in the PUT/SV5 vector was performed by PCR of phagemid pDAN5 scFv clones TS-55 and TS-59. Following PCR, the products were purified, cut with ApaLI and BssHII and ligated in the series of vectors PUT/SV5 cut with the same enzymes. All the PUT/SV5 vectors with either scFv TS-55 and TS-59 were cut with EcoRI and HindIII and ligated into the vector pcDNA3 (Invitrogen, Milan, Italy) cut with the same enzymes.
(viii) HEK293T transfection and selection. The human kidney derived HEK293T cell line was cultured in D-MEM medium (Gibco) supplemented with 10% FCS. Cells were harvested by shaking and plated in a 24 well microtiter plate ($2 \times 10^5$ cells per well). For transient transfection, after 24 h, 1 µg of purified plasmid DNA resuspended in 50 µl of D-MEM without FCS and 2 µl of Lipofectamine 2000 (Invitrogen) in 50 µl of D-MEM were mixed, left at RT for 20 min and added to each well of cultured cells. The cells were grown for further 24/72 h and the supernatant inspected for MB production. Stable cell clones secreting MB were obtained by treating the cells in the same way as for transient transfection, diluting the cells 1:10 with fresh medium 24 h after transfection and adding 400 µg/ml antibiotic G418 (Gibco) for the selection of neomycin resistant cells. After 10 days of culture, the G418 concentration was reduced to 200 µg/ml.
(ix) Transfected HEK293T culture and miniantibody purification. Transfected HEK293T were cultured in D-MEM medium supplemented with 10% FCS previously depleted of IgG using HiTrap Protein G column (Pharmacia). MB derived from 300 ml of supernatant were loaded on another Protein G column and eluted with 1M NaCl in PBS. The fractions were tested for the presence of MB against CD55 and CD59 by ELISA (see section 4.10) and for purity by SDS-PAGE.
(x) ELISA. The antigen reactivity of phages from individual colonies, of soluble scFvs and of MB was evaluated by ELISA as described by Marzari et al (Marzari et al., 2002, Eur J Immunol. 32: 2773-2782). Briefly, microtiter plate wells were coated with purified CD55, CD59 and CD46 (1 µg/100 µl) by overnight incubation in 0.1 M sodium bicarbonate buffer pH 9.6 at 4° C. After saturation with PBS containing 2% non-fat milk (MPBS), the phage suspension or the supernatants containing scFvs or MB were added. The binding of phage was evaluated using 1:3000 anti-phage gene 3 protein conjugated with horseradish peroxidase (Pharmacia Biotech, Milan, Italy) and that of scFv and MB using 1:2000 mAbs anti-SV5 followed by 1:1000 goat anti-mouse Ig conjugated with horse-radish peroxidase (Dako S.p.a. Milan, Italy). All the reactions were revealed using $H_2O_2$ and 3,3',5,5'-tetramethylbenzidine (Sigma-Aldrich) and read at 450 nm.

(xi) Hemolytic assays. To evaluate the neutralizing activity of the MB to CD55 the procedure described by White et al. (White et al., 2004, Protein Sci. 13: 2406-2415) was followed with some modifications. Briefly, a 10% suspension of sheep red blood cells ($3.0 \times 10^9$) sensitized with subagglutinating amount of rabbit IgM (EA) in veronal buffer saline (VBS) was incubated with CD55 (0.3 mg/ml) for 1 h at room temperature, washed, and finally resuspended in VBS to form EA-CD55. Fifty µl of 1% suspension of this erythrocyte intermediate were mixed with 100 µl of each of the two MB or with BRIC216 (0.1 µg/100 µl) prior to addition of 100 µl of 1/100 pooled normal human sera (NHS) and further incubated for 30 min at 37° C. A similar assay was used to test the neutralizing activity of the MB to CD59 except that guinea pig erythrocytes (GPE) were used in the form of the intermediate GPE-CD59. The blocking effect of MB-55 and MB-59 and of the anti-CD59 mAb YTH53.1, used as a positive control, was evaluated by the reactive lysis test using purified C5b6 (2 µg/ml) and 1/1000 C5-deficient serum to form the lytic MAC (Casarsa et al., 2003, Eur J Immunol, 33: 1260-1270).

Lysis of the red cells was evaluated measuring the optical density at 415 nm of the supernatant after removal of intact erythrocytes by centrifugation.

(xii) Immunofluorescence analysis. Lymphoma cells were cultured in RPMI medium (GIBCO) supplemented with 10% FCS. The cells ($5 \times 10^5$) were incubated with the primary mAbs (BRIC216, MB-55, YTH53.1 or MB-59) at 5 µg/ml for 1 h at 37° C. and with the appropriate FITC-conjugated secondary antibodies (Sigma-Aldrich). After washing with the same medium, the cells were fixed with 2% paraformaldehyde (Sigma-Aldrich).

Cell fluorescence was analyzed using a FACScalibur instrument (BD Biosciences) equipped with an air-cooled 15 mW Argon-ion laser, operating at 488 nm. FITC green fluorescence was measured at 530±30 nm bandpass filter. Data were collected using linear amplification for forward and side scatter (FSC and SSC), and logarithmic amplification for FL1. For each sample, 10,000 events were collected and analyzed using CellQuest software (BD Biosciences).

(xiii) Complement-mediated lysis. The procedure of CDC described by Golay et al. (Golay et al., 2000, Blood. 95: 3900-3908) was followed to evaluate the effect of the neutralizing MB on the C susceptibility of Karpas 422 cells with some modifications. Briefly, $2 \times 10^5/50$ µl cells were incubated with Rituximab (R) at 2 µg/ml with or without blocking antibodies (10 µg/ml) to a final volume of 100 µl for 10 min at room temperature prior to the addition of NHS (25%). Residual viable cells were measured after 1 h at 37° C. using MTT assay (Monks et al., J Natl Cancer Inst 1991.83: 757-766).

(xiv) Statistical analysis. The results are expressed, as mean±SD. Statistical significance was determined using the Student's t-test to compare two groups of data.

Example 1

Selection and Characterization of scFvs Anti-Cd55 and Anti-Cd59

Screening of human phage Abs library by ELISA against CD55 and CD59 purified from human red blood cells led to the identification of 4 positive clones for CD55 and 9 positive clones for CD59 after 2 cycles of selection. DNA fingerprinting analysis of the positive clones allowed the recognition of two different clones, each specific for CD55 and CD59, which were named TS-55 for the anti-CD55 and TS-59 for anti-CD59 clone.

The specificity of the selected clones was assessed by ELISA using both phage and soluble scFv (FIG. 1). Each clone reacted strongly with the specific C regulator and did not recognize the other antigen used for selection nor CD46 that served as a negative control. Sequencing of the scFvs revealed that the VH gene for TS-55 derives from the VH3/DP31 gene family/segment, while the VL gene derives from VL3/DPL 16. In the case of TS-59, the VH gene derives from VH3/VH3-48 and the VL gene from VKIV/DPK24.

The coding sequences of the scFvs TS-55 and TS-59 were cloned into a modified version of PUT-SEC vector (Li et al., 1997, Protein Eng. 10: 731-736) containing the Hinge-CH2-CH3 Fc domains of human IgG1 (see materials and methods). After subcloning into pcDNA3, the resulting constructs were transfected into HEK293T cell line and stable clones expressing soluble dimeric miniantibodies (MB) were obtained for both constructs. The reactivity and the specificity of the original scFvs for their specific antigen were confirmed with the MB purified from cell supernatant. The two NB reacting with CD55 and CD59 were named MB-55 and MB-59 respectively and used in all the experiments reported herein.

Example 2

Neutralization of CD55 and CD59 by MB55 and MB-59

Figure 2:
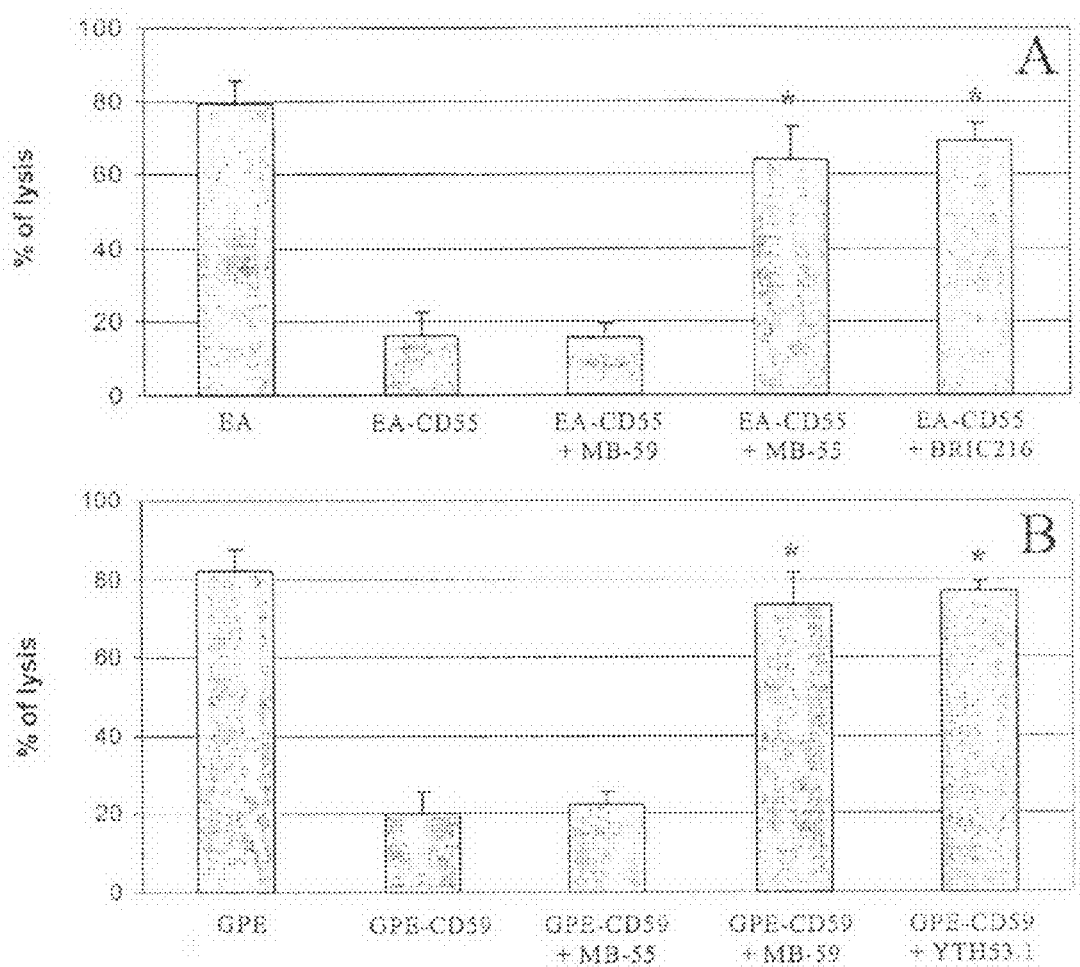
FIGS. 2A-2B show the inhibition of CD55 and CD59 activity by MB-55 and MB-59. Ab-sensitized sheep erythrocytes (EA) were incubated with CD55 for 1 h at room temperature and then mixed with MB-55, MB-59, BRIC 216 or GVBS prior to the addition of normal human serum (FIG. 2A). Guinea pig erythrocytes (GPE) were incubated with CD59 for 1 h at room temperature and then mixed with MB-55, MB-59, YTH53.1 or GVBS prior to addition of C5b6 and C5 deficient serum (FIG. 2B). Data are presented as mean±SD of percent value obtained in three different experiments.* p<0.01 versus control.

Since CD55 and CD59 expressed on the cell surface inhibit C activation and in this way protect the cells from C attack, it was decided to ascertain whether MB-55 and MB-59 directed against these two CRPs were able to neutralize their C inhibitory activity. To this end, Abs-sensitised sheep erythrocytes (EA) and guinea pig erythrocytes (GPE) were rendered resistant to C-dependent lysis following incubation with CD55 and CD59 respectively. To investigate if the MB bad a neutralizing activity for the two CRPs, the two Ab were each incubated with the C-resistant erythrocytes and their ability to restore red cell lysis induced by the C system was evaluated. As shown in FIGS. 2A and 2B, incubation of EA or GPE with the source of C resulted in 80% lysis. This value fell to about 20% when the red cells were incubated with CD55 or CD59 indicating that the two CRPs inhibited C activation. The inhibitory activity of the two CRPs was neutralized by the addition of the corresponding MB, as suggested by the increased lysis observed under these experimental conditions. The value obtained in the presence of the MB was found to be higher than 60% and did not differ from that seen when BRIC216 and YTH53.1, two neutralizing mAb to CD55 and CD59 respectively, were tested in this system. The specificity of the MB was supported by the finding that each of the two MB had a neutralizing effect on the corresponding CRP, but were ineffective on the unrelated CRP.

Example 3

Figure 3:
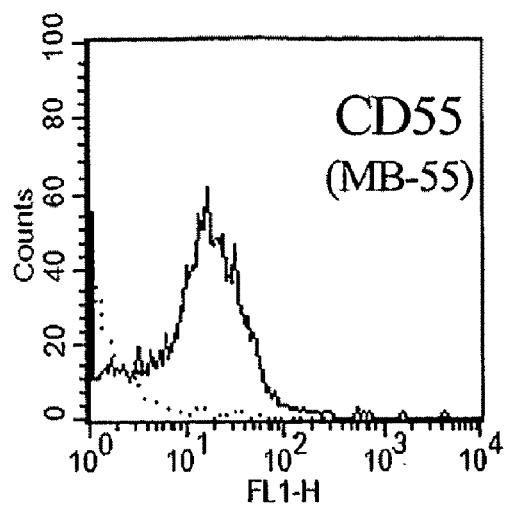
FIG. 3 shows the binding of MB-55 and MB-59 to a B lymphoma cell line by FACS analysis of CD55 and CD59 expression on B lymphoma cell line Karpas 422. The cells were incubated with Abs to CD55 (MB-55 or BRIC216) or with Abs to CD59 (MB-59 or YTH53.1) (-) or with control IgG (••••), followed by the appropriate FITC-labelled secondary antibodies.
Figure 3:
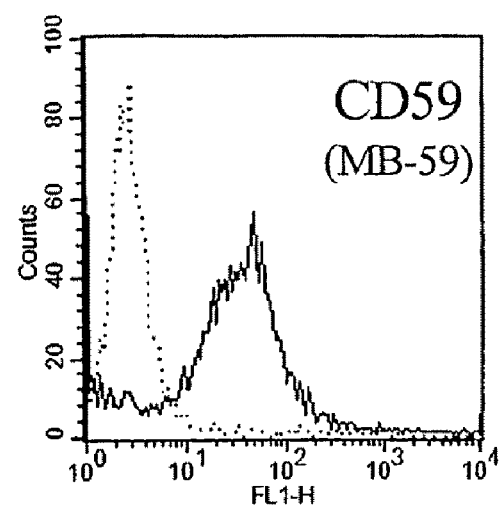
Figure 3:
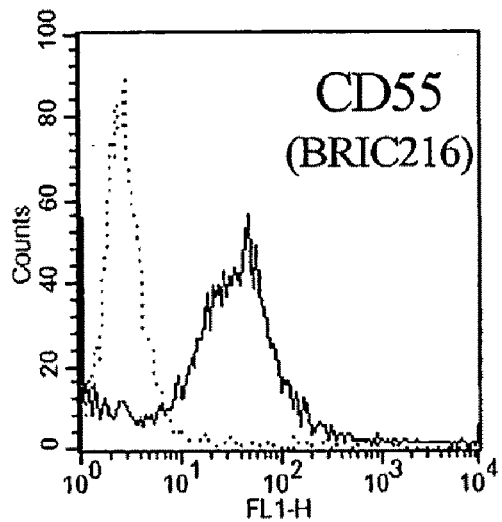
Figure 3:
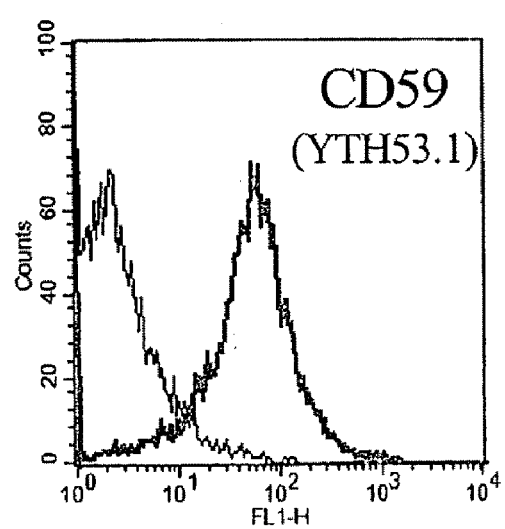

MB-55 and MB-59 bind to a B Lymphoma Cell Line and Promote Rituximab-mediated CDC Having found that the two MB were able to bind to CD55 or CD59 and to neutralize their C-inhibitory activity on red cells, the inventors decided to assess the binding and the effect of these Abs on B lymphoma cell lines. After screening several B lymphoma cell lines, it was decided to use Karpas 422 cells because they express both CD55 and CD59, as evaluated by FACS, using the two mAb BRIC216 and YTH53.1 (FIG. 3). Analysis of MB-55 and MB-59 for their reactivity with Karpas 422 revealed that both MB recognized the two CRPs on the surface of these cells as shown in FIG. 3. The binding specificity of the two MB was confirmed by the failure to detect binding of IgG purified from rat serum to these cells.

Figure 4:
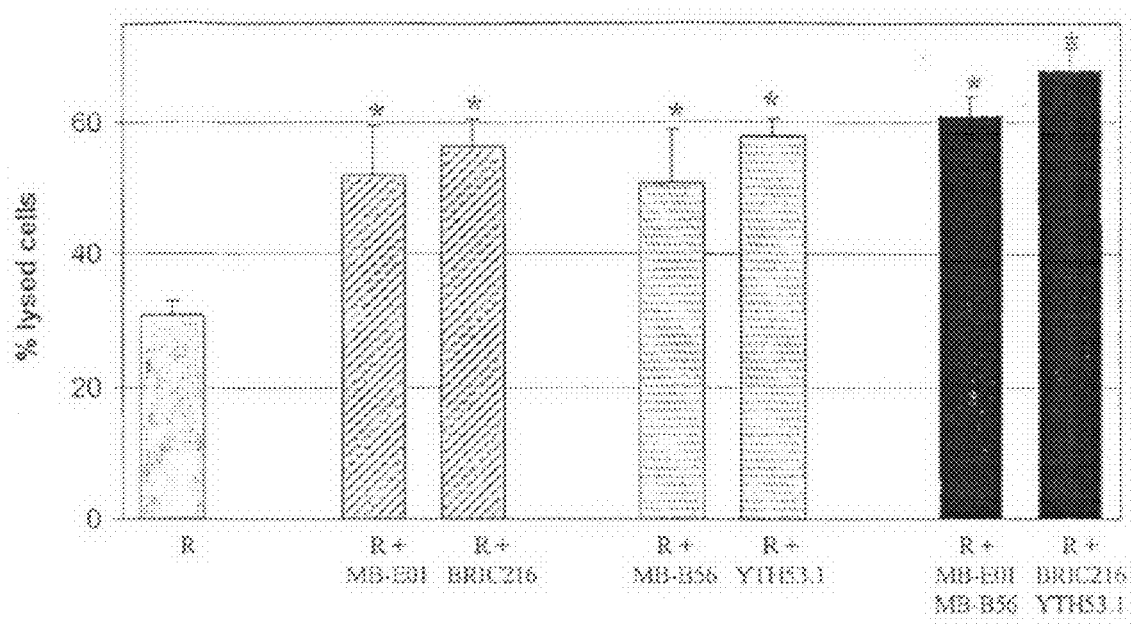
FIG. 4 shows the effect of MB-55 and MB-59 on complement-mediated lysis of Karpas 422. The lymphoma cells ($2 \times 10^5$ cells) were incubated with Rituximab (R, 2 µg/ml) and with each Ab (MB-55, MB-59, BRIC216 and YTH53.1) (10 µg/ml) for 10 min followed by normal human serum (25%). Residual viable cells were measured after 1 h at 37° C. and the number of lysed cells was calculated. Data are presented as mean±SD of percent value obtained in three different experiments. * p<0.01 versus control (R).

To assess the neutralizing activity of MB-55 and MB-59, the effect of these two MB on the susceptibility of Karpas 422 to C-mediated damage stimulated by Rituximab (a humanized mAb to CD20 expressed on this cell line) was evaluated. As previously reported by Golay et al. (Golay et al., 2000, Blood, 95: 3900-3908) and shown in FIG. 4, Karpas 422 cells were found to be relatively resistant to C dependent killing. The number of cells sensitized by Rituximab and killed by C was about 30%, but doubled when each of the two MB was added to the test system and increased slightly following the simultaneous addition of the two MB. As positive controls, BRIC216 and YTH53.1 that also enhanced the C-dependent killing of the cells to an extent similar to that obtained with MB-55 and MB-59 were used. No killing was observed when the MB were incubated with the cells in the absence of Rituximab suggesting that these Abs were unable to activate C.

Example 4

Figure 5:
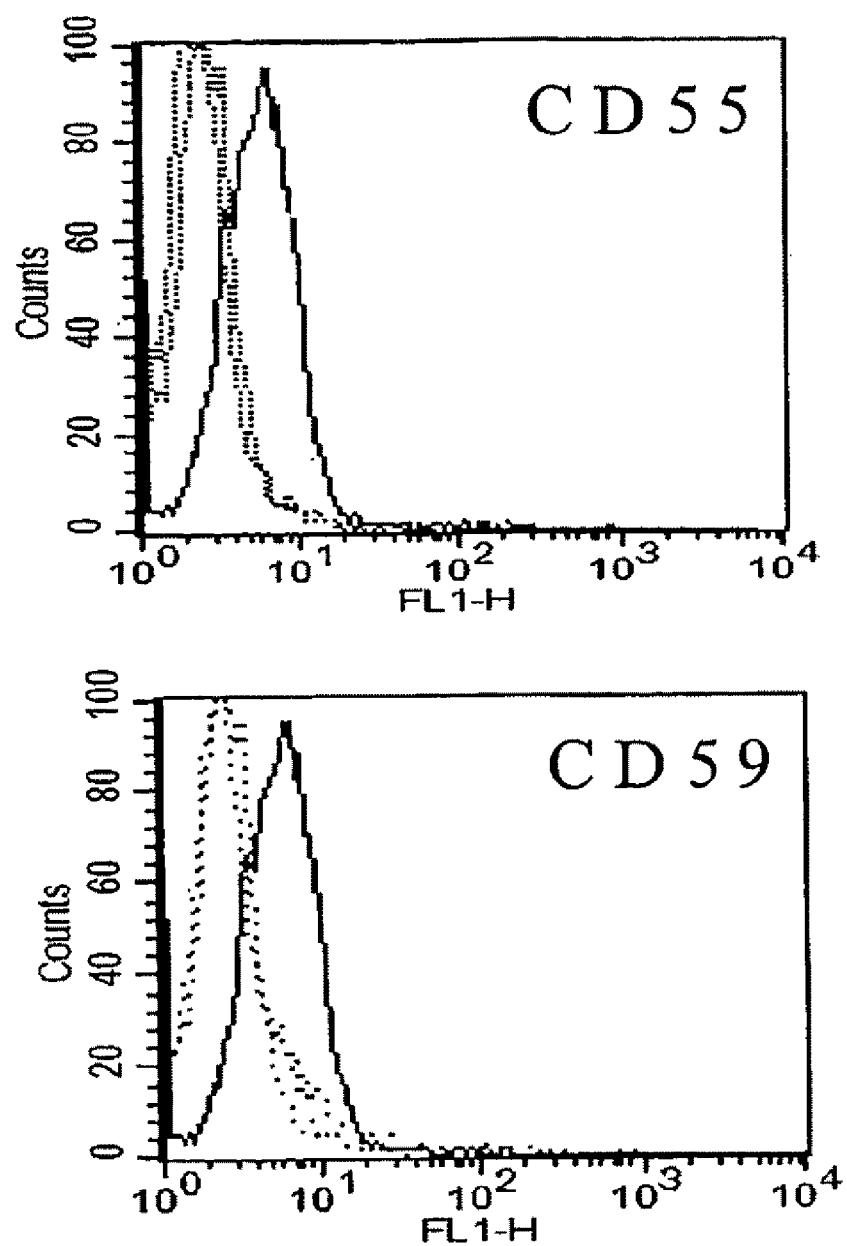
FIG. 5 shows the CD55 and CD59 expression on the surface of transfected HEK293T cells by FACS analysis of HEK293T. Cells transfected with (---) or without (-) MB-55 or MB-59 encoding plasmids were stained by indirect immunoflorescence using BRIC216 for CD55 and YTH53.1 for CD59. The cells treated with control IgG (••••) were used as control.

Decreased Surface Expression of CD55 and CD59 on MB-55 and MB-59 Transfected Cells HEK293T cells were transfected with MB-55 or MB-59 encoding vectors with the aim of producing MB in substantial amounts to be used in all the experiments. Since HEK293T cells are of human embryonic origin, it was decided to analyze these cells for the expression of CD55 and CD59 before and after transfection to ascertain whether the surface expression of these molecule was modulated in transfected cells. As shown in FIG. 5, HEK293T cells tested before transfection reacted with BRIC216 and YTH531.1 as well as with MB-55 and MB-59 indicating that they expressed both CD55 and CD59. Stably transfected producing clones were tested by FACS for the expression of CRP using mAbs BRIC216 and YTH53.1. The results presented in FIG. 5 show that the surface expression of CD55 was efficiently blocked in 81% of cells producing MB-55 and that the expression of CD59 was reduced in 69% of cells producing MB-59. The data obtained on cells examined 48 hours after transfection were essentially similar to those of the stable clones.

Example 5

Construction of Bispecific Antibody Combining Anti-CD20 Minibody with Anti-CD55 or Anti-CD59 Minibodies by Using the "Knob into Hole" system General Description of the Vector:

The genes for the anti-CD55 or the anti CD59 and the anti-CD20 (Rituximab IDEC) scFvs are each cloned into the newly designed vector (pDUO-scFv) for the expression of soluble bispecific minibody molecules.

The pDUO-scFv vector has the backbone of pCDNA3.1Hygro(+) (Invitrogen). In the polylinker the following structures are present (as described in the scheme below):

Kozak sequence
Ig Leader sequence (with minintron)
Scfv-1 (CD55 or CD59)
Human Hinge-$CH_2$—$CH_3$ sequences with the mutation Tyr 67→ Thr
SV5 tag
Furin cutting site
FMDV 2A peptide
Leader sequence
Scfv-2 (anti CD20, Rituximab)
Human hinge $CH_2$—$CH_3$ sequences with the mutation Thr 26→ Tyr
SV5 tag
Stop codon Detailed Description of the pDUO-scFv Vector:

The Leader sequence is composed of 20 amino acids and includes, at the DNA level, also a mini-intron to increase the transcription efficiency. The leader sequence is included to allow secretion of the first minibody molecule into the culture medium.

The ScFv of the CD55/59 is cloned in the VL-Linker-VH orientation.

The Fc region selected is part of the human IgG1 Fc region. It includes the hinge domain and the $CH_2$ and $CH_3$ domains. A single mutation is inserted in the $CH_3$ domain of either the CD55 or the CD59 minibody to create the "knobs-into-holes" configuration. In the Fc region strand the larger $CH_3$ Tyr-67 molecule is converted to a smaller threonine residue by mutating the tyrosine codon, TAT, to the threonine codon, ACC, using PCR primers.

The SV5 tag is included at the end of the Fc region.

A FURIN cleavage site sequence is present. This sequence is 4 amino acids long (RAKR) to allow elimination of the residual 2 amino acid sequence peptide.

A FMDV 2A sequence is taken from the FMDV; it is 24 amino acids long (APVKQTLNFDLLKLAGDVESNPGP) (SEQ ID NO:26) and is efficiently processed in vitro (in HEK 293 cell) and in vivo.

The Leader sequence is composed of 22 amino acids and it is the leader sequence originally used for the secretion of the light chain of the anti-CD20 Rituximab antibody. The leader is included to allow secretion of the molecule into the culture media.

ScFv. The anti CD20 (Rituximab) sequence is cloned in the VL-Linker-VH orientation.

Fc region. The region selected is part of the human IgG1 Fc region. It includes the hinge domain and the $CH_2$ and $CH_3$ domains. A single mutation is inserted in the $CH_3$ domain of the minibody Rituximab to create the "knobs-into-holes" configuration. In this case, the smaller $CH_3$ Thr-26 residue is mutated to a larger tyrosine residue by using PCR primers to change the threonine codon, ACC, to the tyrosine codon TAC.

SV5. The SV5 tag is includes at the end of the Fc region.

Stop Codon

The pDUO-scFv bispecific minibody vector is transiently and stably transfected into HEK 293 cells and CHO cells. Hygromicin is used for the selection of positive HEK 293/CHO cell clones. The fully assembled minibodies are secreted into the culture supernatants. A detailed sequence of the pDUO-scFv vector is listed below as SEQ ID NO: 25.

pDUO-scFv- detailed nucleotide sequence (SEO ID NO: 25):
<u>tctaga</u> tgc cac c ATG GGC TGG AGC CTG ATC CTC CTG TTC CTC GTC GCT GTG GCT ACA G
(XbaI)    (kozak)      (secretory leader)

gtaaggggctcacagtagcaggcttgaggtctggacatatatatgggtgacaatgacatccactttgcctttctctccacag
                              (Mini intron)

GT <u>GTG CAC</u> TCG [SCFVCD55 CD59 SEQUENCE] <u>GCG CGC</u> GACAAAACTCACACATGCCCACCGTGCCCA
   (ApaLI)                                  (BSSH2)         (Hinge)

GCACCTGAACTCCTGGGGGACCGTCAGTCTTCCTCTTCCCCCCAAAACCCAAGGACACCCTCATGATCTCCCGGACCCCTGAGGTCA

CATGCGTGGTGGTGGACGTGAGCCACGAAGACCCTGAGGTCAAGTTCAACTGGTACGTGGACGGCGTGGAGGTGCATAATGCCAAGAC

AAAGCCGCGGGAGGAGCAGTACAACAGCACGTACCGTGTGGTCAGCGTCCTCACCGTCCTGCACCAGGACTGGCTGAATGGCAAGGAG

TACAAGTGCAAGGTCTCCAACAAAGCCCTCCCAGCCCCCATCGAGAAAACCATCTCCAAAGCCAAA

GGGCAGCCCCGAGAACCACAGGTGTACACCCTGCCCCCATCCCGGGAGGAGATGACCAAGAACCAGGTCAGCCTGACCTGCCTGGTCA

AAGGCTTCTATCCCAGCGACATCGCCGTGGAGTGGGAGAGCAATGGGCAGCCGGAGAACAACTACAAGACCACGCCTCCCGTGCTGGA

CTCCGACGGCTCCTTCTTCCTCACCAGCAAGCTCACCGTGGACAAGAGCAGGTGGCAGCAGGGGAACGTCTTCTCATGCTCCGTGATG

CATGAGGCTCTGCACAACCACTACACGCAGAAGAGCCTCTCCCTGTCCCCGGGTAAA
(CH<sub>2</sub>-CH<sub>3</sub>)

<u>ACT AGT</u> GGC AAA CCA ATC CCA AAC CCA CTG CTG GGC CTG GAT <u>AGT ACT</u>
 (SpeI)               (SV5 tag)                          (ScaI)

AgggccaagagaGc<u>accggt</u>gaaacagactttgaattttgaccttctcaagttggcgggagacgtggagtccaacccagggccc
 (Furin site) (AgeI)    (FMDV 2A peptide)

ATGGATTTTCAGGTGCAGATTATCAGCTTCCTGCTAATCAGTGCTTCAGTCATAATGTCCAGAGGG
                              (Leader peptide)

CAAATTGTTCTCTCCCAGTCTCCAGCAATCCTGTCTGCATCTCCAGGGGAGAAGGTCACAATGACTTGCAGGGCCAGCTCAAGTGTAAGTT

ACATCCACTGGTTCCAGCAGAAGCCAGGATCCTCCCCCAAACCCTGGATTTATGCCACATCCAACCTGGCTTCTGGAGTCCCTGTTCGCTT

CAGTGGCAGTGGGTCTGGGACTTCTTACTCTCTCACAATCAGCAGAGTGGAGGCTGAAGATGCTGCCACTTATTACTGCCAGCAGTGGACT

AGTAACCCACCCACGT

<u>TCGGAGGGGGACCAAGCTGGAAATCAAATCCGGAGGGTCGACCATAACTTCGTATAATGTATACTATACGAAGTTATCCTCGAGCGGTAC

C</u>

CAGGTACAACTGCAGCAGCCTGGGGCTGAGCTGGTGAAGCCTGGGGCCTCAGTGAAGATGTCCTGCAAGGCTTCTGGCTACACATTTACCA

GTTACAATATGCACTGGGTAAAACAGACACCTGGTCGGGGCCTGGAATGGATTGGAGCTATTTATCCCGGAAATGGTGATACTTCCTACAA

TCAGAAGTTCAAAGGCAAGGCCACATTGACTGCAGACAAATCCTCCAGCACAGCCTACATGCAGCTCAGCAGCCTGACATCTGAGGACTCT

GCGGTCTATTACTGTGCAAGATCGACTTACTACGGCGGTGACTGGTACTTCAATGTCTGGGGCGCAGGGACCACCGTCACCGTCTCTGCA
(RITUXIMAB SEQUENCE)

<u>GCT AGC</u> GACAAAACTCACACATGCCCACCGTGCCCA
(Nhe I)    (Hinge)

GCACCTGAACTCCTGGGGGACCGTCAGTCTTCCTCTTCCCCCCAAAACCCAAGGACACCCTCATGATCTCCCGGACCCCTGAGGTCA

CATGCGTGGTGGTGGACGTGAGCCACGAAGACCCTGAGGTCAAGTTCAACTGGTACGTGGACGGCGTGGAGGTGCATAATGCCAAGAC

AAAGCCGCGGGAGGAGCAGTACAACAGCACGTACCGTGTGGTCAGCGTCCTCACCGTCCTGCACCAGGACTGGCTGAATGGCAAGGAG

TACAAGTGCAAGGTCTCCAACAAAGCCCTCCCAGCCCCCATCGAGAAAACCATCTCCAAAGCCAAA

GGGCAGCCCCGAGAACCACAGGTGTACACCCTGCCCCCATCCCGGGAGGAGATGACCAAGAACCAGGTCAGCCTGTACTGCCTGGTCAAAG

GCTTCTATCCCAGCGACATCGCCGTGGAGTGGGAGAGCAATGGGCAGCCGGAGAACAACTACAAGACCACGCCTCCCGTGCTGGACTCCGA

CGGCTCCTTCTTCCTCTATAGCAAGCTCACCGTGGACAAGAGCAGGTGGCAGCAGGGGAACGTCTTCTCATGCTCCGTGATGCATGAGGCT

CTGCACAACCACTACACGCAGAAGAGCCTCTCCCTGTCCCCCGGTAAA
(CH<sub>2</sub>-CH<sub>3</sub>)

<u>ACT AGT</u> GGC AAA CCA ATC CCA AAC CCA CTG CTG GGC CTG GAT <u>AGT ACT</u> TAA <u>AAG CTT</u>
 (SpeI)               (SV5 tag)                          (ScaI) (Stop)(HindIII)

Example 6

Figure 6:
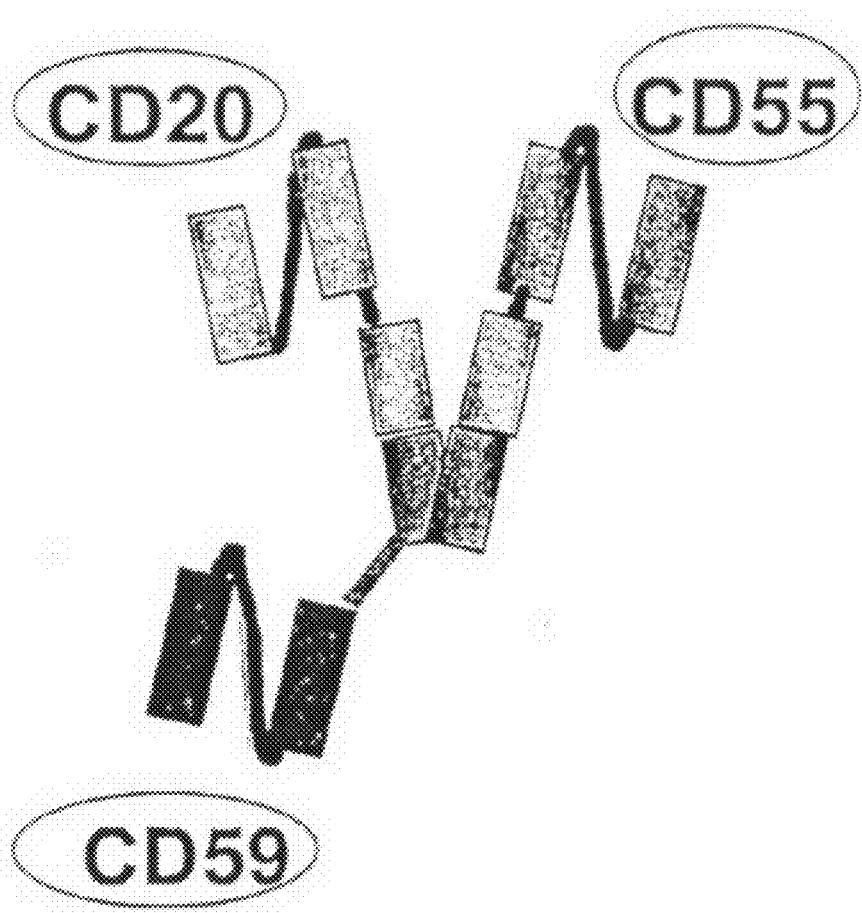
FIG. 6 demonstrates the construction of trispecific antibodies combining anti-CD20 minibody with anti-CD55 and anti-CD59 minibodies.

Construction of Trispecific Antibodies Combining Anti-CD20 Minibody with Anti-CD55 and Anti-CD59 Minibodies Trispecific antibodies are produced using the pTRIS vector (a modified version of the pDUO vector). As illustrated in FIG. 6, the pTRIS vector contains the general structure of the pDUO vector with the following differences: the third antibody specificity (anti CD55 or CD59) is cloned in the scFv format 3' to the CH3 domain of the pre-existing anti-CD20 binding arm. In particular, the SV5 tag and the stop codon at the end of the second arm are substituted with a 24 aa linker sequence followed by the third scFv fragment, the SV5 tag and a stop codon.

Example 7

Targeting Lymphoma Cells (LCL2) in vitro Using MB-55 and MB-59 Minibodies in Combination with Rituximab Rituximab, MB55 and MB59 antibodies were biotin labeled and were used in an in vitro complement-dependent killing assay using LCL2 lymphoma cells. The results of the in vitro assay are demonstrated in FIG. 7. The LCL2 lymphoma cells were treated with the following antibodies: (i) biotin-labeled Rituximab alone (Rit-bio, left column) for one hour; (ii) biotin-labeled Rituximab antibodies with biotin-labeled MB55 and MB59 minibodies for one hour (Rit-bio+MB-bio, second column from the left); (iii) biotin-labeled Rituximab antibodies for one hour followed by avidin in the second hour and than with biotin-labeled minibodies (Rit-bio+avidin+MB-bio, third column from the left). The right column represents the results obtained with Red blood cells treated with biotin-labeled Rituximab antibodies for one hour followed by avidin in the second hour and than with biotin-labeled minibodies (E Rit-bio+avidin+MB-bio, right column). Following the incubation with the antibodies, human serum was added (25%) for 1 h. The percent of lysed cells was determined using the MTT assay.

Figure 7:
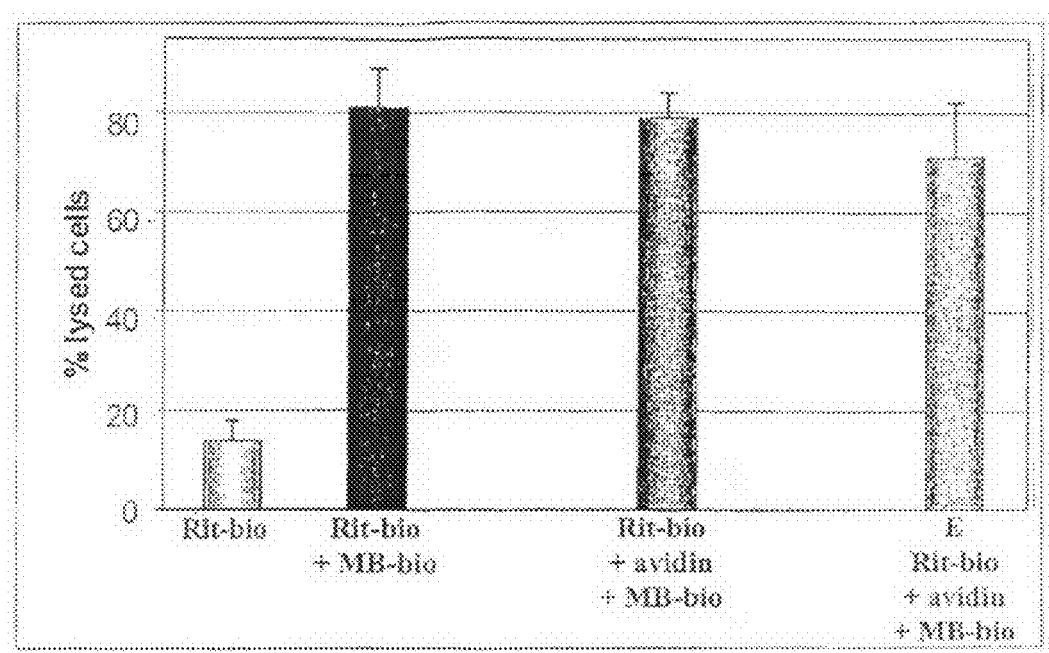
FIG. 7 demonstrates the targeting of lymphoma cells (LCL2) in vitro using MB-55 and MB-59 minibodies in combination with Rituximab.

As revealed from the results demonstrated in FIG. 7, the treatment with biotin-labeled Rituximab antibodies and biotin-labeled M55 and MB59 minibodies was significantly more effective than the treatment with biotin-labeled Rituximab alone in both LCL2 lymphoma cells and Red blood cells.

Example 8

In vivo Effect of Rituximab and Anti-CD55 and Anti-CD59 Minibodies in the Treatment of Lymphoma In order to examine the in vivo effect of Rituximab and the anti-CD55 and anti-CD59 minibodies in the treatment of lymphoma, the following animal model was established: LCL-2 lymphoma cells ($1.5 \times 10^6$) were injected intra-peritoneally in SCID inbred mice at day 0. These mice are homozygous for the $Prkdc^{scid}$ mutation and lack both T and B cells due to a defect in V(D)J recombination. Therefore, they easily accept foreign tissue transplants, including human tumors. Following the injection of the LCL-2 lymphoma cells, the animals were treated in four groups (six animals per group) as following: (i) Rituximab-biotin antibodies (25 µg); (ii) anti-CD55-biotin and anti-CD59-biotin minibodies (100 µg); (iii) Rituximab-biotin antibodies (25 µg), Avidin (40 µg) and anti-CD55-biotin and anti-CD59-biotin minibodies (100 µg); and (iv) Saline. The antibody injections were carried out at days 4 and 11 post LCL-2 lymphoma cells injection and the survival of the mice was monitored over time.

Figure 8:
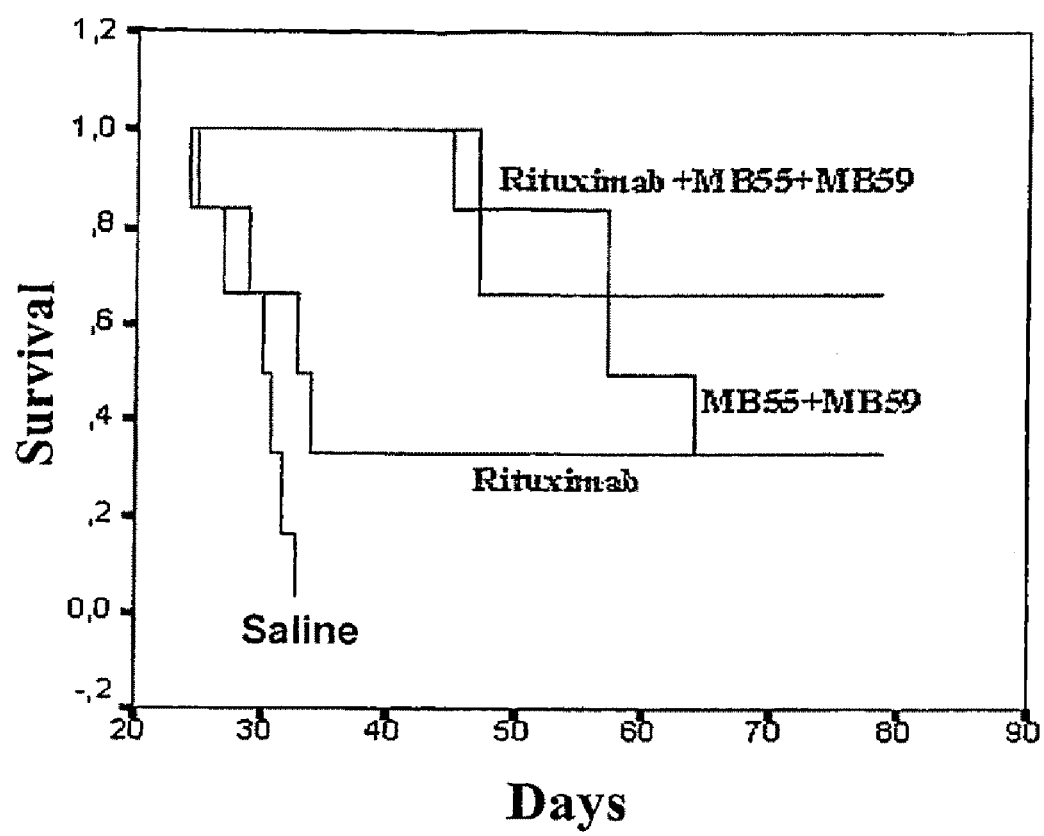
FIG. 8 shows the in vivo effect of Rituximab and anti-CD55 and anti-CD59 minibodies in the treatment of lymphoma.

The survival of the animals was demonstrated using the Kaplan-Mayer survival curve (FIG. 8). As revealed from the results, animals treated with biotin-labeled Rituximab antibodies and biotin-labeled MB55 and MB59 minibodies showed significantly better survival as compared to the animals treated with biotin-labeled Rituximab alone or with biotin-labeled MB55 and MB59 minibodies.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

The invention claimed is:

1. A recombinant antibody comprising an antigen binding region which comprises a heavy chain variable region ($V_H$) and a light chain variable region ($V_L$), wherein the amino acid sequence of the $V_H$ comprises the amino acid sequence set forth in SEQ ID NO: 6 and the amino acid sequence of the $V_L$ comprises the amino acid sequence set forth in SEQ ID NO: 2; and
wherein the antibody binds and neutralizes the complement inhibitory activity of the complement (C) regulatory protein CD59.

2. The recombinant antibody of claim 1 which is a single-chain antibody fragment (scFv), wherein the $V_L$ and $V_H$ are operatively attached by a linker.

3. The recombinant antibody of claim 2, further comprising a human IgG1 constant domain.

4. A pharmaceutical composition comprising as an active ingredient the recombinant antibody of claim 1 and a pharmaceutically acceptable carrier.

5. The recombinant antibody of claim 1 which is a bispecific antibody, wherein the CD59 antigen-binding region is operatively attached to a second antigen-binding region that binds to a tumor-specific antigen overexpressed in tumor cells.

6. A recombinant antibody which is a heterodimeric molecule, comprising: (a) a first single chain antibody fragment comprising a light chain variable region ($V_L$) and a heavy chain variable region ($V_H$) of a CD59 antibody operatively attached to each other by a linker, the first single chain antibody fragment being operatively attached to a human $CH_2$ constant domain and a human $CH_3$ constant domain, and (b) a second single chain antibody fragment comprising a $V_L$ and a $V_H$ of a CD20 antibody operatively attached to each other by a linker, the second single chain antibody fragment being operatively attached to a human $CH_2$ constant domain and a human $CH_3$ constant domain, wherein the $V_L$ of the CD59 antibody comprises the amino acid sequence set forth in SEQ ID NO: 2 and the $V_H$ of the CD59 antibody comprises the amino acid sequence set forth in SEQ ID NO: 6.

7. A pharmaceutical composition comprising the heterodimeric molecule of claim 6 and a pharmaceutically acceptable carrier.

8. The bispecific antibody of claim 5 wherein the second antigen-binding region comprises a CD55 antigen-binding region.

9. The bispecific antibody of claim 5 wherein the second antigen-binding region comprises a CD20 antigen-binding region.

10. The bispecific antibody of claim 9 wherein the CD20 antigen-binding region is specific for the CD20 epitope expressed on cancer cells.

11. A pharmaceutical composition comprising the bispecific antibody of any of claim 5, 8, 9, or 10 and a pharmaceutically acceptable carrier.

12. The recombinant antibody of claim 6, wherein the $CH_3$ domain attached to the first single chain antibody fragment differs from the $CH_3$ domain attached to the second single chain antibody fragment.

13. The recombinant antibody of claim 12, wherein both $CH_3$ domains comprise a mutation to promote heterodimerization.

14. A method for treating a lymphoma in a subject, comprising administering a therapeutically effective dose of the pharmaceutical composition according to claim 7 to the subject.

* * * * *